United States Patent
Gurin et al.

(10) Patent No.: US 11,301,552 B2
(45) Date of Patent: Apr. 12, 2022

(54) MEDICAL DEVICE WITH INTEGRATED ULTRASONIC AUTHENTICATION

(71) Applicant: InvenSense, Inc., San Jose, CA (US)

(72) Inventors: Ilya Gurin, San Jose, CA (US); Karthik Katingari, San Jose, CA (US)

(73) Assignee: InvenSense, Inc., San Jose, CA (US)

( * ) Notice: Subject to any disclaimer, the term of this patent is extended or adjusted under 35 U.S.C. 154(b) by 349 days.

(21) Appl. No.: 16/223,116

(22) Filed: Dec. 18, 2018

(65) Prior Publication Data

US 2019/0188365 A1 Jun. 20, 2019

Related U.S. Application Data

(60) Provisional application No. 62/607,155, filed on Dec. 18, 2017.

(51) Int. Cl.
| | |
|---|---|
| *H04L 29/06* | (2006.01) |
| *G06F 15/16* | (2006.01) |
| *G06F 7/04* | (2006.01) |
| *G06F 21/32* | (2013.01) |
| *G16H 10/60* | (2018.01) |
| *G16H 40/63* | (2018.01) |
| *G06K 9/00* | (2022.01) |

(52) U.S. Cl.
CPC ............ *G06F 21/32* (2013.01); *G16H 10/60* (2018.01); *G16H 40/63* (2018.01); *G06K 9/0002* (2013.01)

(58) Field of Classification Search
CPC ......... G06F 21/32; G16H 10/60; G16H 40/63
USPC .............................................. 726/8
See application file for complete search history.

(56) References Cited

U.S. PATENT DOCUMENTS

| | | | |
|---|---|---|---|
| 9,089,270 B2* | 7/2015 | Song | A61B 5/389 |
| 2014/0148104 A1* | 5/2014 | Marterstock | A61B 5/4866 |
| | | | 455/73 |
| 2015/0241393 A1* | 8/2015 | Ganti | G01N 29/09 |
| | | | 73/589 |
| 2017/0231534 A1* | 8/2017 | Agassy | G06K 9/0002 |
| | | | 382/124 |
| 2020/0218817 A1* | 7/2020 | Thrower | G06F 21/6218 |

OTHER PUBLICATIONS

David Gregorczyk; A Proof of Concept for Medical Device Integration using Web Services; IEEE:2007; p. 1-6.*

* cited by examiner

*Primary Examiner* — Monjur Rahim

(57) ABSTRACT

A medical device comprises a surface, an ultrasonic sensor, and a processor. The surface is configured to interact with skin of a patient during operation of the medical device. The ultrasonic sensor is disposed beneath the surface and configured to ultrasonically measure data with respect to a region above the surface. The processor is coupled with the ultrasonic sensor. Responsive to detection of a finger in contact with the surface, the processor is configured to operate the ultrasonic sensor to capture a fingerprint of the finger. Responsive to authentication that a person associated with the captured fingerprint is authorized to use the medical device, the processor is configured to activate operation of the medical device.

28 Claims, 18 Drawing Sheets

1400

```
┌─────────────────────────────────────────────────────────────────┐
│  DETECT A FINGER IN CONTACT WITH A PORTION OF THE MEDICAL DEVICE │
│                              1410                                │
└─────────────────────────────────────────────────────────────────┘
                                │
                                ▼
┌─────────────────────────────────────────────────────────────────┐
│  RESPONSIVE TO DETECTING THE FINGER, CAPTURE, WITH AN ULTRASONIC │
│   SENSOR DISPOSED BENEATH THE PORTION OF THE MEDICAL DEVICE, A   │
│   FINGERPRINT OF THE FINGER WHILE THE FINGER IS IN CONTACT WITH  │
│              THE PORTION OF THE MEDICAL DEVICE                   │
│                              1420                                │
└─────────────────────────────────────────────────────────────────┘
                                │
                                ▼
┌─────────────────────────────────────────────────────────────────┐
│   RESPONSIVE TO AUTHENTICATING THAT A PERSON ASSOCIATED WITH THE │
│    CAPTURED FINGERPRINT IS AUTHORIZED TO USE THE MEDICAL DEVICE, │
│              ACTIVATE OPERATION OF THE MEDICAL DEVICE            │
│                              1430                                │
└─────────────────────────────────────────────────────────────────┘
```

┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ AUTHENTICATE THAT THE PERSON ASSOCIATED WITH THE CAPTURED FINGERPRINT │
│              IS AUTHORIZED TO USE THE MEDICAL DEVICE               │
│                             1440                                   │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘

ASSOCIATE A MEASUREMENT MADE BY THE MEDICAL DEVICE, WHILE ACTIVATED, WITH ONE OF THE CAPTURED FINGERPRINT AND THE PERSON
1470

1400 continued

DETERMINE A CONTACT CHARACTERISTIC FROM THE CAPTURED FINGERPRINT
1480

EMPLOY THE CONTACT CHARACTERISTIC TO ENABLE OR DISABLE THE ACTIVATION OF THE MEDICAL DEVICE
1485

1500

```
DETECT A FINGER IN CONTACT WITH A PORTION OF THE MEDICAL DEVICE
1510
```
↓
```
RESPONSIVE TO DETECTING THE FINGER, CAPTURE, WITH AN ULTRASONIC
SENSOR DISPOSED BENEATH THE PORTION OF THE MEDICAL DEVICE, A
FINGERPRINT OF THE FINGER WHILE THE FINGER IS IN CONTACT WITH THE
PORTION OF THE MEDICAL DEVICE
1520
```
↓
```
RESPONSIVE TO IDENTIFICATION OF A PERSON ASSOCIATED WITH THE
FINGERPRINT, ACTIVATE OPERATION OF THE MEDICAL DEVICE
1530
```

( 1530 )
↓
```
IDENTIFY THE PERSON ASSOCIATED WITH THE FINGERPRINT
1540
```

ASSOCIATE A MEASUREMENT MADE BY THE MEDICAL DEVICE, WHILE ACTIVATED, WITH ONE OF THE CAPTURED FINGERPRINT AND THE PERSON
1570

1500 continued

DETERMINE A CONTACT CHARACTERISTIC FROM THE CAPTURED FINGERPRINT
1580

EMPLOY THE CONTACT CHARACTERISTIC TO ENABLE OR DISABLE THE ACTIVATION OF THE MEDICAL DEVICE
1585

MEDICAL DEVICE WITH INTEGRATED ULTRASONIC AUTHENTICATION

CROSS REFERENCE TO RELATED APPLICATIONS—PROVISIONAL

This application claims priority to and benefit of U.S. Provisional Patent Application No. 62/607,155 filed on Dec. 18, 2017 entitled "MEDICAL DEVICE WITH INTEGRATED ULTRASONIC AUTHENTICATION" by Ilya Gurin and Karthik Katingari, which is assigned to the assignee of the present application. The disclosure of U.S. Provisional Patent Application No. 62/607,155 is hereby incorporated herein by reference in its entirety.

CROSS REFERENCE TO RELATED APPLICATIONS

This application is related to co-pending U.S. patent application Ser. No. 15/354,876 filed on Nov. 17, 2016 entitled "OPERATING A FINGERPRINT SENSOR COMPRISED OF ULTRASONIC TRANSDUCERS" by Salvia et al., assigned to the assignee of the present application. To the extent not repeated herein, the contents of related U.S. patent application Ser. No. 15/354,876 are hereby incorporated herein by reference.

This application is related to co-pending U.S. patent application Ser. No. 15/205,743 filed on Jul. 8, 2016 entitled "PIEZOELECTRIC MICROMACHINED ULTRASONIC TRANSDUCER (PMUT)" by Eldwin Ng et al., assigned to the assignee of the present application. To the extent not repeated herein, the contents of related U.S. patent application Ser. No. 15/205,743 are hereby incorporated herein by reference.

This application is related to co-pending U.S. patent application Ser. No. 15/266,673 filed on Sep. 15, 2016 entitled "OPERATING A TWO-DIMENSIONAL ARRAY OF ULTRASONIC TRANSDUCERS" by Nikhil Apte et al., assigned to the assignee of the present application. To the extent not repeated herein, the contents of related U.S. patent application Ser. No. 15/266,673 are hereby incorporated herein by reference.

BACKGROUND

Many medical devices exist which operate by a user/patient touching a surface on the medical device with a portion of their skin, so that the medical device may take some type of medical measurement. For example, skin of a patient interacts with an electrode during the conduct of an electrocardiogram (EKG) or an electroencephalogram (EEG), interacts with a light emitter and receiver during photoplethysmography, or with a lancet/needle-stick-device during sampling blood (such for glucose monitoring). The portion of skin often used is a finger. Medical devices which perform these, and other types of medical measurements may be human portable (i.e., of hand-holdable size) or else have been miniaturized to the point that a user may utilize them at home and sometimes even as a function of a mobile electronic device such as a smart wristwatch or a smart phone.

BRIEF DESCRIPTION OF DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

FIGS. 14A-14F illustrate a flow diagram of an example method of operating a medical device, in accordance with various embodiments.

FIGS. 15A-15F illustrate a flow diagram of an example method of operating a medical device, in accordance with various embodiments.

DESCRIPTION OF EMBODIMENTS

Figure 1A:
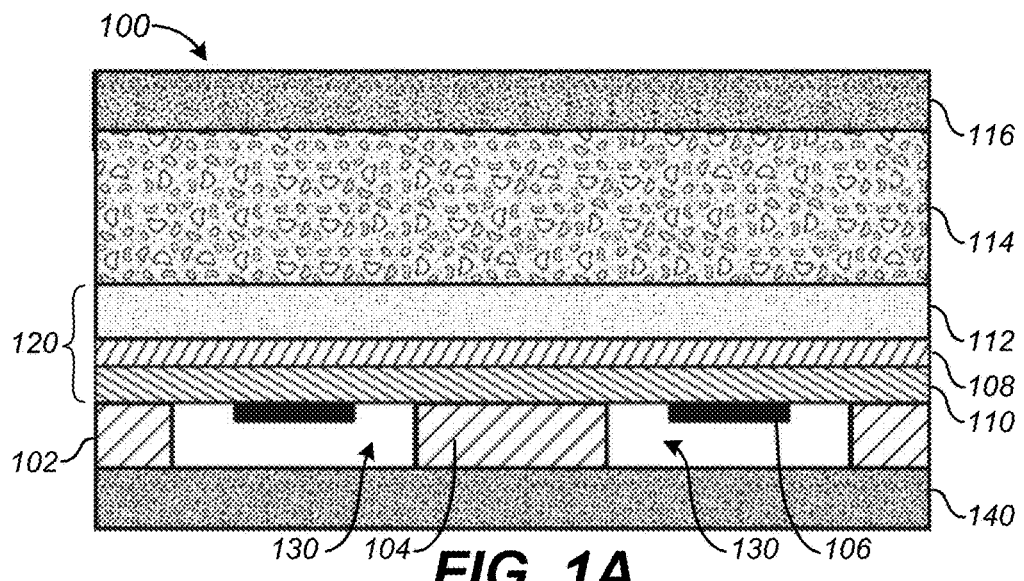
FIG. 1A is a diagram illustrating a piezoelectric micromachined ultrasonic transducer (PMUT) device having a center pinned membrane, according to some embodiments.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Notation and Nomenclature

Some portions of the detailed descriptions which follow are presented in terms of procedures, logic blocks, processing and other symbolic representations of operations on data within an electrical device. These descriptions and representations are the means used by those skilled in the data processing arts to most effectively convey the substance of their work to others skilled in the art. In the present application, a procedure, logic block, process, or the like, is conceived to be one or more self-consistent procedures or instructions leading to a desired result. The procedures are those requiring physical manipulations of physical quantities. Usually, although not necessarily, these quantities take the form of acoustic (e.g., ultrasonic) signals capable of being transmitted and received by an electronic device and/or electrical or magnetic signals capable of being stored, transferred, combined, compared, and otherwise manipulated in an electrical device.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "capturing," "generating," "determining," "receiving," "comparing," "selecting," "acquiring," "providing," "proceeding," "controlling," "detecting," "capturing," "authenticating," "activating," "associating," "measuring," "operating," or the like, refer to the actions and processes of an electronic device such as an electrical device.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, logic, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the example fingerprint sensing system and/or mobile electronic device described herein may include components other than those shown, including well-known components.

Various techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, perform one or more of the methods described herein. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

Various embodiments described herein may be executed by one or more processors, such as one or more motion processing units (MPUs), sensor processing units (SPUs), sensor processor(s), host processor(s) or core(s) thereof, digital signal processors (DSPs), general purpose microprocessors, application specific integrated circuits (ASICs), application specific instruction set processors (ASIPs), field programmable gate arrays (FPGAs), a programmable logic controller (PLC), a complex programmable logic device (CPLD), a discrete gate or transistor logic, discrete hardware components, or any combination thereof designed to perform the functions described herein, or other equivalent integrated or discrete logic circuitry. The term "processor," as used herein may refer to any of the foregoing structures or any other structure suitable for implementation of the techniques described herein. As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Moreover, processors can exploit nano-scale architectures such as, but not limited to, molecular and quantum-dot based transistors, switches and gates, in order to optimize space usage or enhance performance of user equipment. A processor may also be implemented as a combination of computing processing units.

In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an SPU/MPU and a microprocessor, a plurality of microprocessors, one or more microprocessors in conjunction with an SPU core, MPU core, or any other such configuration.

It is to be noted that, as used in this specification and the appended claims, the singular forms "a," "an," and "the" include plural referents unless the context clearly dictates otherwise. Also, any reference herein to "top," "bottom," "upper," "lower," "up," "down," "front," "back," "first," "second," "left," or "right" is not intended to be a limitation herein. It is appreciated that, in the following description, numerous specific details are set forth to provide a thorough understanding of the examples. However, it is appreciated that the examples may be practiced without limitation to these specific details. In other instances, well-known methods and structures may not be described in detail to avoid unnecessarily obscuring the description of the examples. Also, the examples may be used in combination with each other.

Overview of Discussion

Discussion is divided into three sections. In Section One, discussion begins with a description of an example piezoelectric micromachined ultrasonic transducer (PMUT), in accordance with various embodiments. Example sensors including arrays of ultrasonic transducers are then described. In Section Two, an ultrasonic fingerprint sensor which utilizes an array of PMUTs for fingerprint sensing is described along with an example array of PMUTS. In Section Three, several example medical devices with integrated ultrasonic authentication are described along with methods of authenticating use and operating the medical devices.

Conventionally, many medical devices had been developed that operate by touching a surface of the device to a patient's skin and then taking a measurement while in contact with the patient's skin. Some such devices include the EEG, the EKG, the photoplethysmograph, the pulse/heartrate monitor, and various needlestick devices that use a microneedle lancet or array thereof for withdrawing interstitial fluid (e.g., to measure blood glucose). As many of these devices are portable and/or wearable, patients may keep them at home or take the devices with them as they travel about. In many instances, medical professionals may utilize measurements from these devices to monitor and/or diagnose a patient, even though the devices may be used outside of a hospital/clinic in an unmedically-controlled environment. As described herein, ultrasonic fingerprint sensors may be integrated with various medical devices to authenticate that a measurement made by a medical device is associated with the fingerprint of a particular patient.

In some embodiments, this may involve storing the measurements in a manner linked to a fingerprint acquired in conjunction with capturing a measurement. In some embodiments, this may involve authenticating a patient (via a fingerprint) before activating a medical device to take a measurement from the authenticated patient. In this manner, measurements made by a medical device may be authenticated as being acquired from a particular patient, rather than from a family member or other person who may be trying out a medical device or may be trying to fake and/or sabotage a measurement.

Additionally, as some medical devices require particular positioning or contact to make an accurate measurement, the described ultrasonic fingerprint sensors may be utilized to authenticate proper positioning and/or contact with skin (such as of finger) prior to activating a medical device to capture a measurement, or during the measurement to make sure proper positioning and/or contact with the skin is maintained. This authentication of proper positioning and/or contact reduces artifacts which may be introduced during medical measurements in the absence of trained medical device operators. Additionally, an image of the finger positioning may be stored with measured data for later analysis.

Further, moisture on or in the skin of a patient can confound conventional skin/finger detection technologies such as electrical sensing or capacitive sensing, however ultrasonic sensing is unaffected by such moisture allowing it to function well with wet or moist skin.

Further still, when a medical device requires direct electrical contact with the skin of a patient (such as an EKG), capacitive or other conventional electrical sensing of a finger or fingerprint may interfere with the sensing, while ultrasonic sensing as described herein will not cause such interference as it uses sound waves rather than electrical signals and the sound waves are at a much higher frequency than that of electrical sensors used in typical medical devices. Furthermore, conventional capacitive and optical sensing technologies cannot be disposed beneath a metal electrode, opposite the side which makes contact with the skin of a patient, as these technologies cannot sense through the metal of the electrode. However, as described herein, an ultrasonic sensor may be disposed beneath a conductive skin contact electrode (which may be a metal electrode) of a medical device and acoustically detect skin, presence of a finger, and/or a fingerprint with ultrasonic sound waves are not impeded by the conductive contact electrode.

Although embodiments are described in relation to specific ultrasonic sensor architectures, it should be appreciated that different types of ultrasonic fingerprint sensors having different architectures may be utilized herein. For instance, some architectures include an array of ultrasonic transducers (e.g., PMUTs), embodiments of which are described herein. However, the described medical device embodiments may utilize other ultrasonic architectures. For example, in some embodiments bulk mode ultrasonic transducers or piezoelectric film-based sensors may also utilized in the techniques described herein.

Section One: Example Ultrasonic Architecture

Systems and methods disclosed herein, in one or more aspects provide efficient structures for an acoustic transducer (e.g., a piezoelectric actuated transducer or PMUT). One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. In addition, the word "example" is used herein to mean serving as an example, instance, or illustration.

FIG. 1A is a diagram illustrating a PMUT device 100 having a center pinned membrane, according to some embodiments. PMUT device 100 includes an interior pinned membrane 120 positioned over a substrate 140 to define a cavity 130. In one embodiment, membrane 120 is attached both to a surrounding edge support 102 and interior support 104. In one embodiment, edge support 102 is connected to an electric potential. Edge support 102 and interior support 104 may be made of electrically conducting materials, such as and without limitation, aluminum, molybdenum, or titanium. Edge support 102 and interior support 104 may also be made of dielectric materials, such as silicon dioxide, silicon nitride or aluminum oxide that have electrical connections the sides or in vias through edge support 102 or interior support 104, electrically coupling lower electrode 106 to electrical wiring in substrate 140.

In one embodiment, both edge support 102 and interior support 104 are attached to a substrate 140. In various embodiments, substrate 140 may include at least one of, and without limitation, silicon or silicon nitride. It should be appreciated that substrate 140 may include electrical wirings and connection, such as aluminum or copper. In one embodiment, substrate 140 includes a CMOS logic wafer bonded to edge support 102 and interior support 104. In one embodiment, the membrane 120 comprises multiple layers. In an example embodiment, the membrane 120 includes lower electrode 106, piezoelectric layer 110, and upper electrode 108, where lower electrode 106 and upper electrode 108 are coupled to opposing sides of piezoelectric layer 110. As shown, lower electrode 106 is coupled to a lower surface of piezoelectric layer 110 and upper electrode 108 is coupled to an upper surface of piezoelectric layer 110. It should be appreciated that, in various embodiments, PMUT device 100 is a microelectromechanical (MEMS) device.

In one embodiment, membrane 120 also includes a mechanical support layer 112 (e.g., stiffening layer) to mechanically stiffen the layers. In various embodiments, mechanical support layer 112 may include at least one of, and without limitation, silicon, silicon oxide, silicon nitride, aluminum, molybdenum, titanium, etc. In one embodiment, PMUT device 100 also includes an acoustic coupling layer 114 above membrane 120 for supporting transmission of acoustic signals. It should be appreciated that acoustic coupling layer can include air, liquid, gel-like materials, or other materials for supporting transmission of acoustic signals. In one embodiment, PMUT device 100 also includes platen layer 116 above acoustic coupling layer 114 for containing acoustic coupling layer 114 and providing a contact surface for a finger or other sensed object with PMUT device 100. It should be appreciated that, in various embodiments, acoustic coupling layer 114 provides a contact surface, such that platen layer 116 is optional. Moreover, it should be appreciated that acoustic coupling layer 114 and/or platen layer 116 may be included with or used in conjunction with multiple PMUT devices. For example, an array of PMUT devices may be coupled with a single acoustic coupling layer 114 and/or platen layer 116.

Figure 1B:
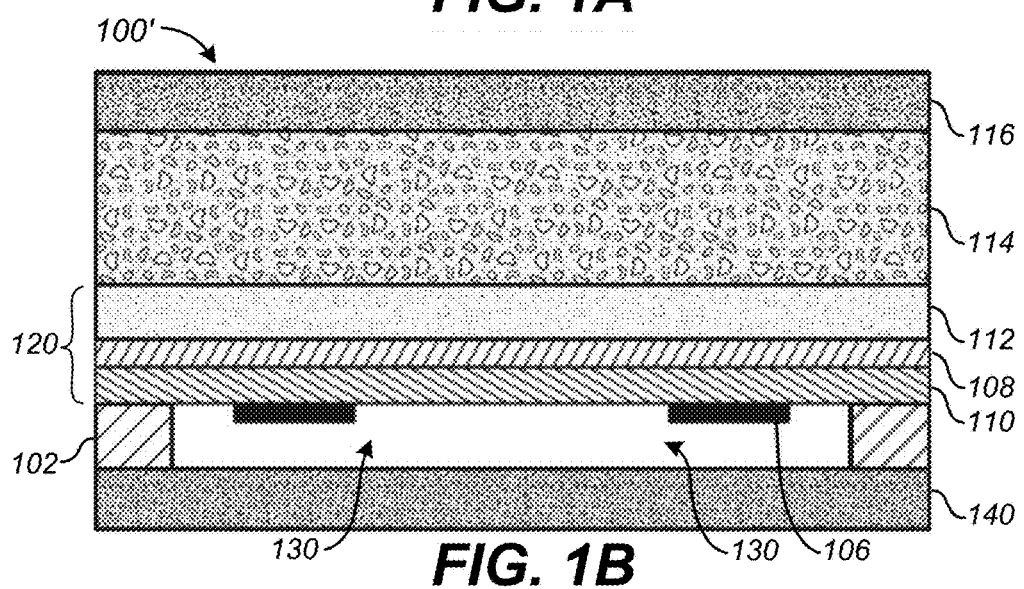
FIG. 1B is a diagram illustrating a PMUT device having an unpinned membrane, according to some embodiments.

FIG. 1B is identical to FIG. 1A in every way, except that the PMUT device 100' of FIG. 1B omits the interior support 104 and thus membrane 120 is not pinned (e.g., is "unpinned"). There may be instances in which an unpinned membrane 120 is desired. However, in other instances, a pinned membrane 120 may be employed.

Figure 2:
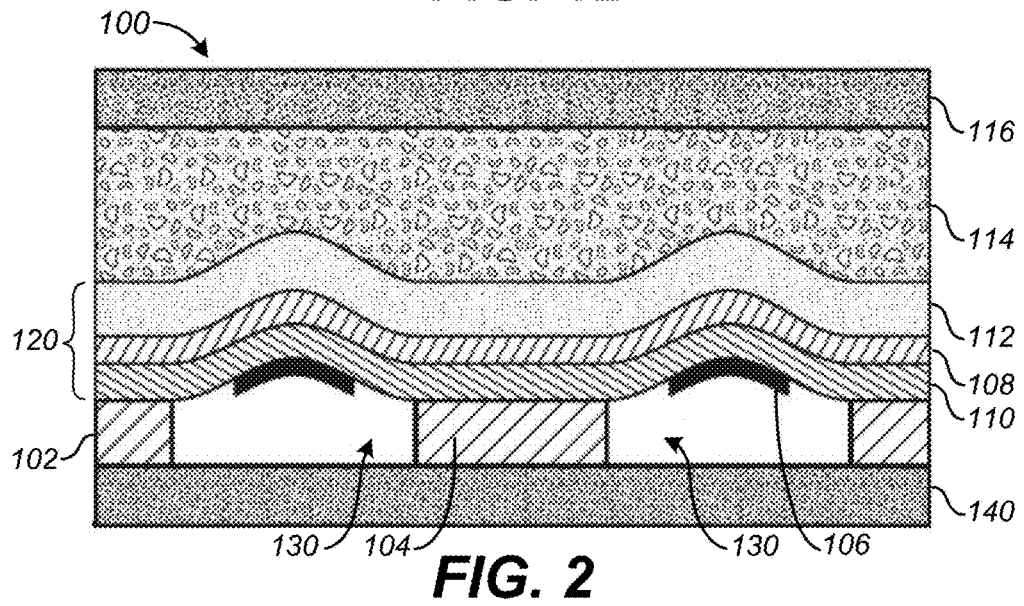
FIG. 2 is a diagram illustrating an example of membrane movement during activation of a PMUT device having a center pinned membrane, according to some embodiments.

FIG. 2 is a diagram illustrating an example of membrane movement during activation of pinned PMUT device 100, according to some embodiments. As illustrated with respect to FIG. 2, in operation, responsive to an object proximate platen layer 116, the electrodes 106 and 108 deliver a high frequency electric charge to the piezoelectric layer 110, causing those portions of the membrane 120 not pinned to the surrounding edge support 102 or interior support 104 to be displaced upward into the acoustic coupling layer 114. This generates a pressure wave that can be used for signal probing of the object. Return echoes can be detected as pressure waves causing movement of the membrane, with compression of the piezoelectric material in the membrane causing an electrical signal proportional to amplitude of the pressure wave.

The described PMUT device 100 can be used with almost any electrical device that converts a pressure wave into mechanical vibrations and/or electrical signals. In one aspect, the PMUT device 100 can comprise an acoustic sensing element (e.g., a piezoelectric element) that generates and senses ultrasonic sound waves. An object in a path of the generated sound waves can create a disturbance (e.g., changes in frequency or phase, reflection signal, echoes, etc.) that can then be sensed. The interference can be analyzed to determine physical parameters such as (but not limited to) distance, density and/or speed of the object. As an example, the PMUT device 100 can be utilized in various applications, such as, but not limited to, fingerprint or physiologic sensors suitable for wireless devices, industrial systems, automotive systems, robotics, telecommunications, security, medical devices, etc. For example, the PMUT device 100 can be part of a sensor array comprising a plurality of ultrasonic transducers deposited on a wafer, along with various logic, control and communication electronics. A sensor array may comprise homogenous or identical PMUT devices 100, or a number of different or heterogonous device structures.

In various embodiments, the PMUT device 100 employs a piezoelectric layer 110, comprised of materials such as, but not limited to, aluminum nitride (AlN), lead zirconate titanate (PZT), quartz, polyvinylidene fluoride (PVDF), and/or zinc oxide, to facilitate both acoustic signal production and sensing. The piezoelectric layer 110 can generate electric charges under mechanical stress and conversely experience a mechanical strain in the presence of an electric field. For example, the piezoelectric layer 110 can sense mechanical vibrations caused by an ultrasonic signal and produce an electrical charge at the frequency (e.g., ultrasonic frequency) of the vibrations. Additionally, the piezoelectric layer 110 can generate an ultrasonic wave by vibrating in an oscillatory fashion that might be at the same frequency (e.g., ultrasonic frequency) as an input current generated by an alternating current (AC) voltage applied across the piezoelectric layer 110. It should be appreciated that the piezoelectric layer 110 can include almost any material (or combination of materials) that exhibits piezoelectric properties, such that the structure of the material does not have a center of symmetry and a tensile or compressive stress applied to the material alters the separation between positive and negative charge sites in a cell causing a polarization at the surface of the material. The polarization is directly proportional to the applied stress and is direction dependent so that compressive and tensile stresses results in electric fields of opposite polarizations.

Further, the PMUT device 100 comprises electrodes 106 and 108 that supply and/or collect the electrical charge to/from the piezoelectric layer 110. It should be appreciated that electrodes 106 and 108 can be continuous and/or patterned electrodes (e.g., in a continuous layer and/or a patterned layer). For example, as illustrated, electrode 106 is a patterned electrode and electrode 108 is a continuous electrode. As an example, electrodes 106 and 108 can be comprised of almost any metal layers, such as, but not limited to, aluminum (Al)/titanium (Ti), molybdenum (Mo), etc., which are coupled with and on opposing sides of the piezoelectric layer 110.

According to an embodiment, the acoustic impedance of acoustic coupling layer 114 is selected to be similar to the acoustic impedance of the platen layer 116, such that the acoustic wave is efficiently propagated to/from the membrane 120 through acoustic coupling layer 114 and platen layer 116. As an example, the platen layer 116 can comprise various materials having an acoustic impedance in the range between 0.8 to 4 mega-Rayleigh (MRayl), such as, but not limited to, plastic, resin, rubber, Teflon, epoxy, etc. In another example, the platen layer 116 can comprise various materials having a high acoustic impedance (e.g., an acoustic impendence greater than 10 MRayl), such as, but not limited to, glass, aluminum-based alloys, sapphire, etc. Typically, the platen layer 116 can be selected based on an application of the sensor. For instance, in fingerprinting applications, platen layer 116 can have an acoustic impedance that matches (e.g., exactly or approximately) the acoustic impedance of human skin (e.g., $1.6 \times 10^6$ Rayl). Further, in one aspect, the platen layer 116 can further include a thin layer of anti-scratch material. In various embodiments, the anti-scratch layer of the platen layer 116 is less than the wavelength of the acoustic wave that is to be generated and/or sensed to provide minimum interference during propagation of the acoustic wave. As an example, the anti-scratch layer can comprise various hard and scratch-resistant materials (e.g., having a Mohs hardness of over 7 on the Mohs scale), such as, but not limited to sapphire, glass, titanium nitride (TiN), silicon carbide (SiC), diamond, etc. As an example, PMUT device 100 can operate at 20 MHz and accordingly, the wavelength of the acoustic wave propagating through the acoustic coupling layer 114 and platen layer 116 can be 70-150 microns. In this example scenario, insertion loss can be reduced and acoustic wave propagation efficiency can be improved by utilizing an anti-scratch layer having a thickness of 1 micron and the platen layer 116 as a whole having a thickness of 1-2 millimeters. It is noted that the term "anti-scratch material" as used herein relates to a material that is resistant to scratches and/or scratch-proof and provides substantial protection against scratch marks.

In accordance with various embodiments, the PMUT device 100 can include metal layers (e.g., aluminum (Al)/titanium (Ti), molybdenum (Mo), etc.) patterned to form electrode 106 in particular shapes (e.g., ring, circle, square, octagon, hexagon, etc.) that are defined in-plane with the membrane 120. Electrodes can be placed at a maximum strain area of the membrane 120 or placed at close to either or both the surrounding edge support 102 and interior support 104. Furthermore, in one example, electrode 108 can be formed as a continuous layer providing a ground plane in contact with mechanical support layer 112, which can be formed from silicon or other suitable mechanical stiffening material. In still other embodiments, the electrode 106 can be routed along the interior support 104, advantageously reducing parasitic capacitance as compared to routing along the edge support 102.

For example, when actuation voltage is applied to the electrodes, the membrane 120 will deform and move out of plane. The motion then pushes the acoustic coupling layer 114 it is in contact with and an acoustic (ultrasonic) wave is generated. Oftentimes, vacuum is present inside the cavity 130 and therefore damping contributed from the media within the cavity 130 can be ignored. However, the acoustic coupling layer 114 on the other side of the membrane 120 can substantially change the damping of the PMUT device 100. For example, a quality factor greater than 20 can be observed when the PMUT device 100 is operating in air with atmosphere pressure (e.g., acoustic coupling layer 114 is air) and can decrease lower than 2 if the PMUT device 100 is operating in water (e.g., acoustic coupling layer 114 is water).

Figure 3:
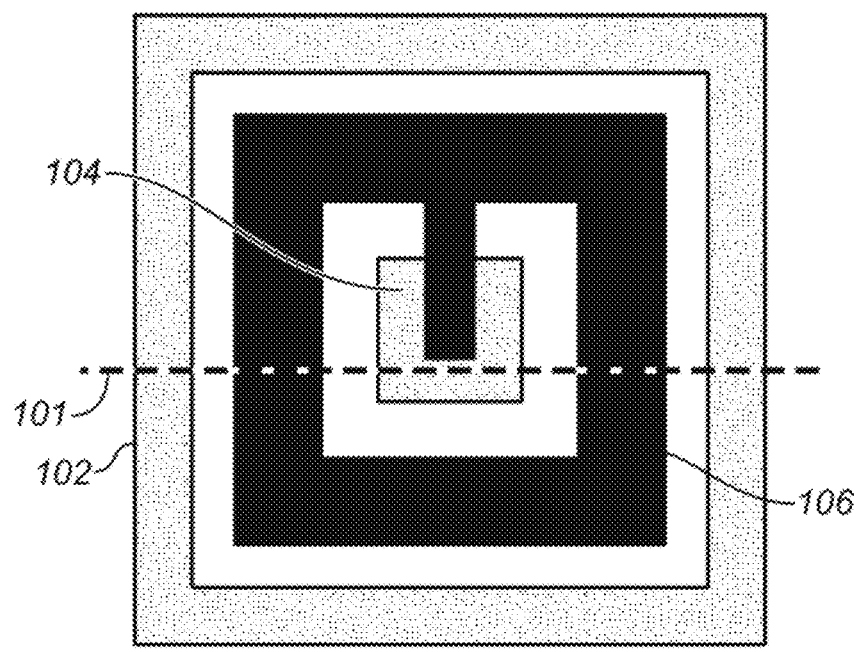
FIG. 3 is a top view of the PMUT device of FIG. 1A, according to some embodiments.

FIG. 3 is a top view of the PMUT device 100 of FIG. 1A having a substantially square shape, which corresponds in part to a cross section along dotted line 101 in FIG. 3. Layout of surrounding edge support 102, interior support 104, and lower electrode 106 are illustrated, with other continuous layers not shown. It should be appreciated that the term "substantially" in "substantially square shape" is intended to convey that a PMUT device 100 is generally square-shaped, with allowances for variations due to manufacturing processes and tolerances, and that slight deviation from a square shape (e.g., rounded corners, slightly wavering lines, deviations from perfectly orthogonal corners or intersections, etc.) may be present in a manufactured device. While a generally square arrangement PMUT device is shown, alternative embodiments including rectangular, hexagon, octagonal, circular, or elliptical are contemplated. In other embodiments, more complex electrode or PMUT device shapes can be used, including irregular and non-symmetric layouts such as chevrons or pentagons for edge support and electrodes.

Figure 4:
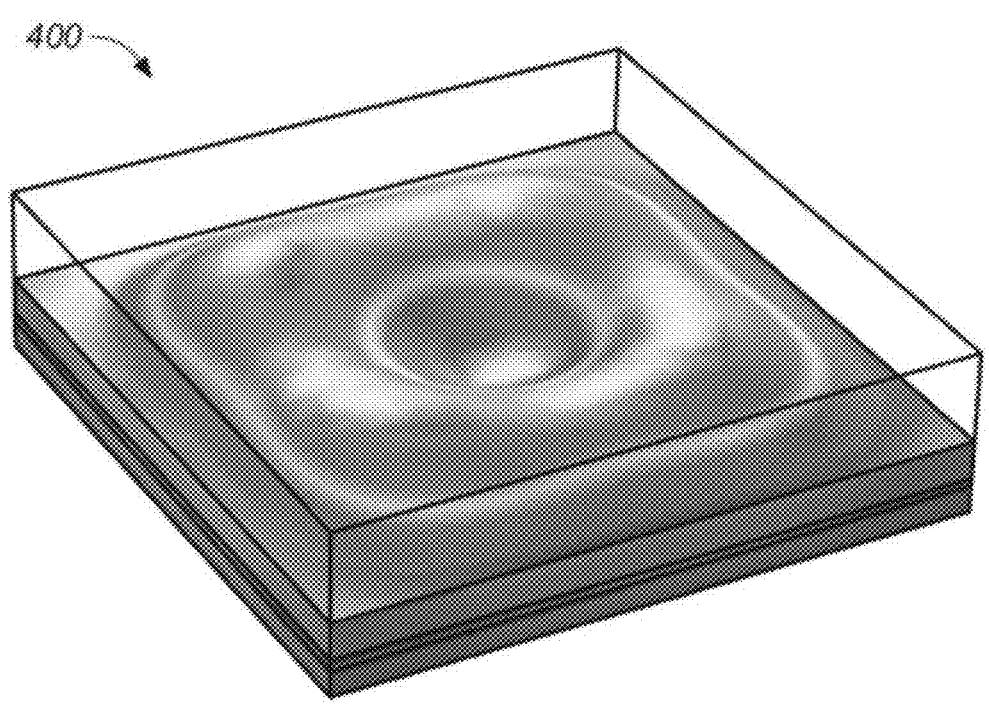
FIG. 4 is a simulated map illustrating maximum vertical displacement of the membrane of the PMUT device shown in FIGS. 1A, 2, and 3, according to some embodiments.

FIG. 4 is a simulated topographic map 400 illustrating maximum vertical displacement of the membrane 120 of the PMUT device 100 shown in FIGS. 1A-3. As indicated, maximum displacement generally occurs along a substantially circular center axis of the lower electrode, with corner regions having the greatest displacement. As with the other figures, FIG. 4 is not drawn to scale with the vertical displacement exaggerated for illustrative purposes, and the maximum vertical displacement is a fraction of the horizontal surface area comprising the PMUT device 100. In an example PMUT device 100, maximum vertical displacement may be measured in nanometers, while surface area of an individual PMUT device 100 may be measured in square microns.

Figure 5:
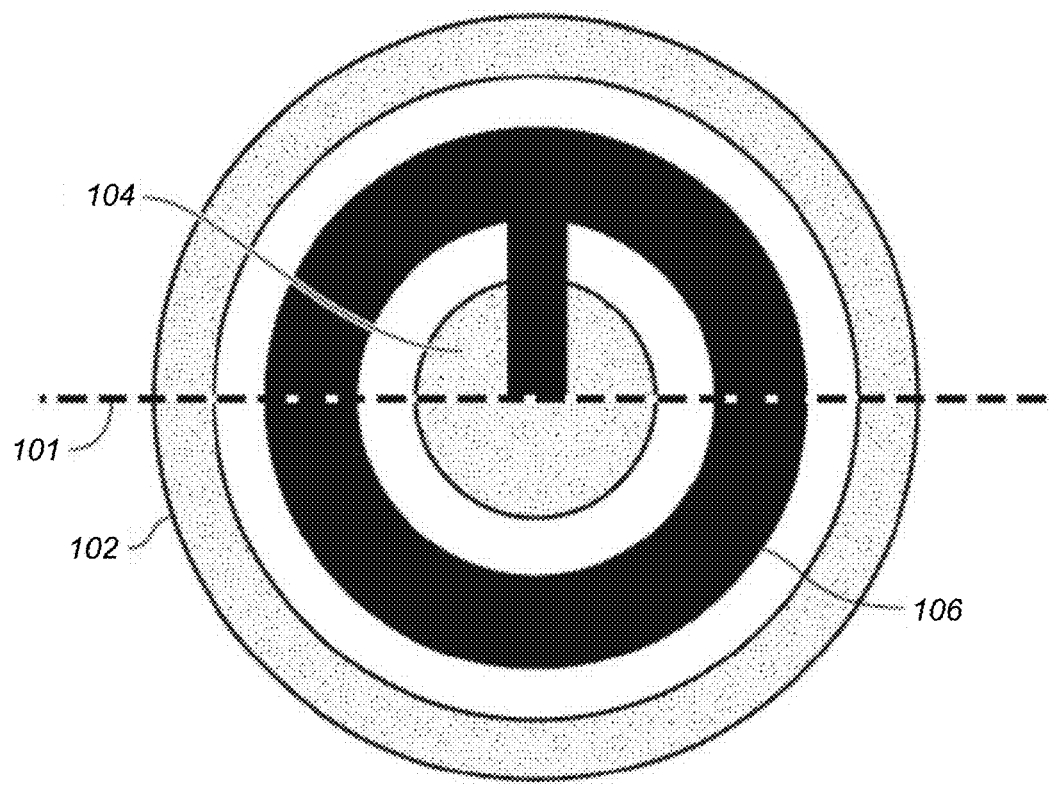
FIG. 5 is a top view of an example PMUT device having a circular shape, according to some embodiments.

FIG. 5 is a top view of another example of the PMUT device 100 of FIG. 1A having a substantially circular shape, which corresponds in part to a cross section along dotted line 101 in FIG. 5. Layout of surrounding edge support 102, interior support 104, and lower electrode 106 are illustrated, with other continuous layers not shown. It should be appreciated that the term "substantially" in "substantially circular shape" is intended to convey that a PMUT device 100 is generally circle-shaped, with allowances for variations due to manufacturing processes and tolerances, and that slight deviation from a circle shape (e.g., slight deviations on radial distance from center, etc.) may be present in a manufactured device.

Figure 6:
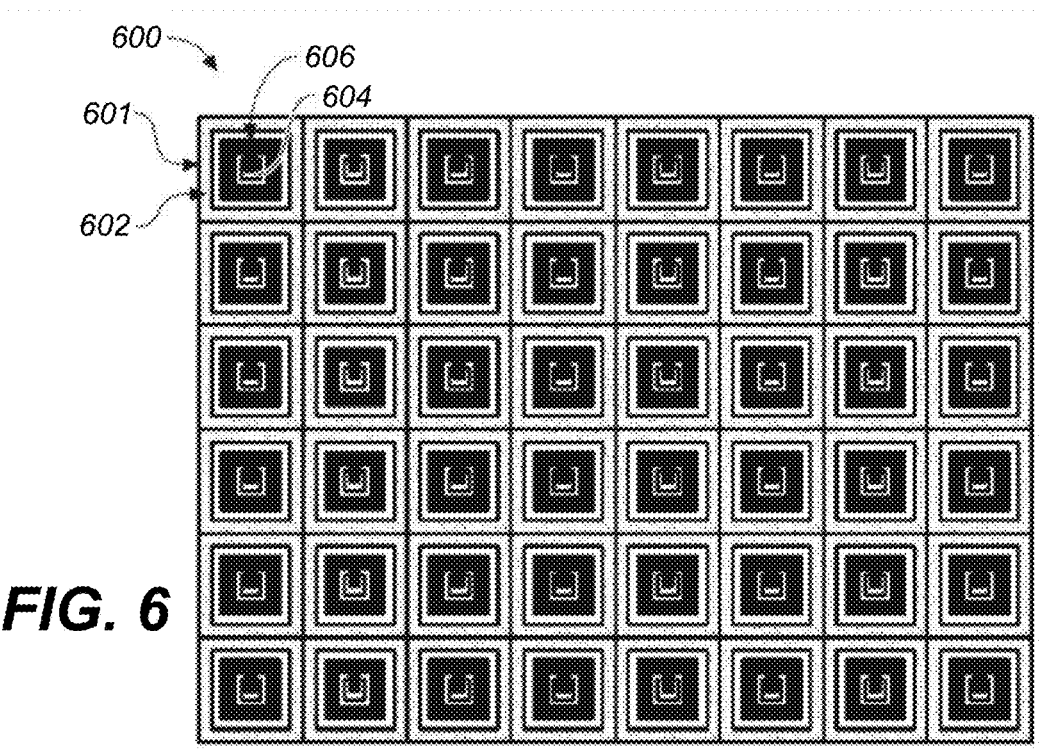
FIG. 6 illustrates an example array of square-shaped PMUT devices, according to some embodiments.

FIG. 6 illustrates an example two-dimensional array 600 of square-shaped PMUT devices 601 formed from PMUT devices having a substantially square shape similar to that discussed in conjunction with FIGS. 1A, 1B, 2, and 3. That is, a PMUT 601, may be the same or similar to PMUT 100 or 100' in some embodiments. Layout of square surrounding edge support 602, interior support 604, and square-shaped lower electrode 606 surrounding the interior support 604 are illustrated, while other continuous layers are not shown for clarity. As illustrated, array 600 includes square-shaped PMUT devices 601 that are in rows and columns. It should be appreciated that rows or columns of the square-shaped PMUT devices 601 may be offset. Moreover, it should be appreciated that square-shaped PMUT devices 601 may contact each other or be spaced apart. In various embodiments, adjacent square-shaped PMUT devices 601 are electrically isolated. In other embodiments, groups of adjacent square-shaped PMUT devices 601 are electrically connected, where the groups of adjacent square-shaped PMUT devices 601 are electrically isolated.

In operation, during transmission, selected sets of PMUT devices in the two-dimensional array can transmit an acoustic signal (e.g., a short ultrasonic pulse) and during sensing, the set(s) of active PMUT devices in the two-dimensional array can detect an interference of the acoustic signal with an object (in the path of the acoustic wave). The received interference signal (e.g., generated based on reflections, echoes, etc. of the acoustic signal from the object) can then be analyzed. As an example, an image of the object, a distance of the object from the sensing component, a density of the object, a motion of the object, etc., can all be determined based on comparing a frequency and/or phase of the interference signal with a frequency and/or phase of the acoustic signal. A PMUT 601 in an array, such as array 600, may ultrasonically capture a pixel or portion of a pixel which, when combined with other pixels captured by the array, for an ultrasonically generated image of the object (i.e., a finger) in the path of the acoustic wave(s). In this manner, a fingerprint may be imaged from the varying depths of its ridges on a finger sensed by the array of PMUTs. Moreover, results generated can be further analyzed or presented to a user via a display device (not shown).

Section Two: Ultrasonic Fingerprint Sensor

Figure 7A:
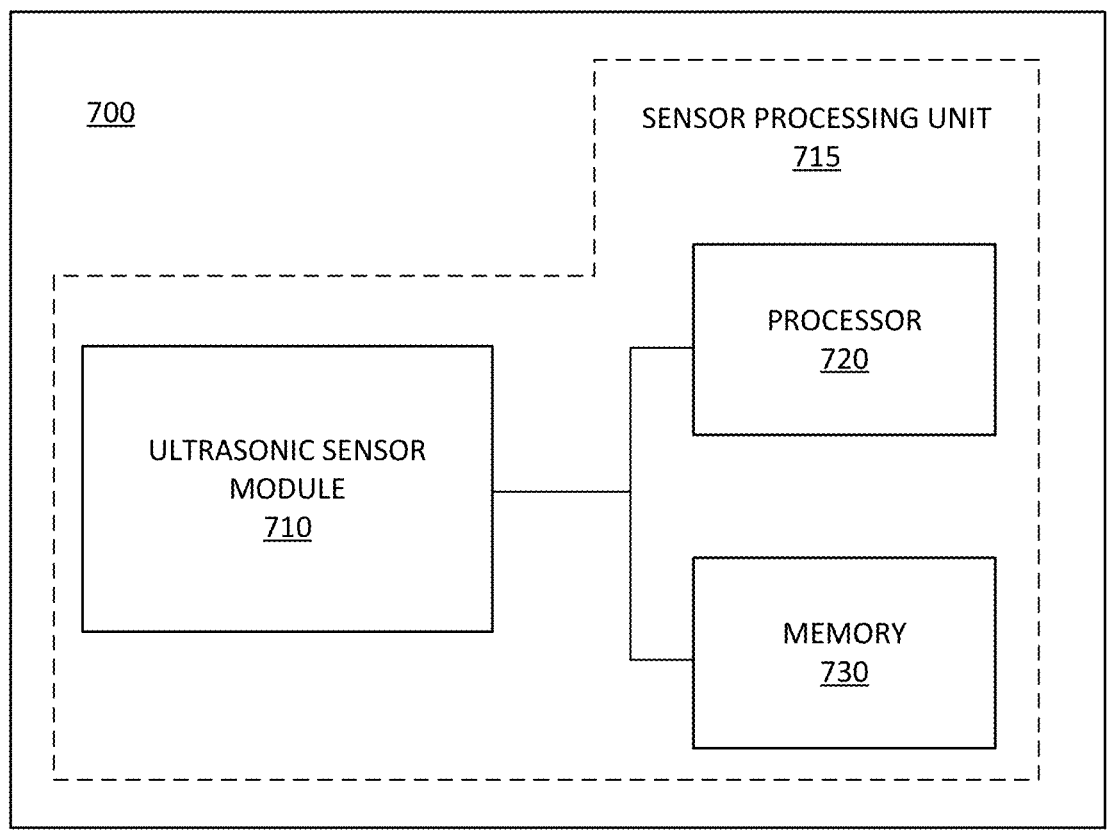
FIG. 7A illustrates an example fingerprint sensor, in accordance with various embodiments.

FIG. 7A illustrates an example fingerprint sensor 700, in accordance with various embodiments. In one embodiment, fingerprint sensor 700 includes an ultrasonic sensor module 710, a processor 720, and a memory 730.

Processor 720 can be any type of suitable processor. Processor 720 may be, without limitation, one or more microprocessors, CPUs, DSPs, general purpose microprocessors, ASICs, ASIPs, FPGAs or other processors which run software programs, which may be stored in a memory, such as memory 730.

Memory 730 can be any suitable type of memory, including but not limited to electronic memory (e.g., read only memory (ROM), random access memory, or other electronic memory). Memory 730 may store algorithms or routines or other instructions for processing data received from one or more sensors (e.g., from ultrasonic sensor module 710) as well as the received data either in its raw form or after some processing. Such algorithms and routines may be implemented by processor 720 and/or by logic or processing capabilities included a sensor.

Processor 720 and memory 730 may be portions of a sensor processing unit 715 which may be integrated with fingerprint sensor 700. In such a case processor 720 is considered a sensor processor. It should be appreciated that components of fingerprint sensor 700 are examples, and that certain components, such as processor 720 and/or memory 730 may or may not be located within fingerprint sensor 700. For example, always on or system circuitry of an electronic device which includes fingerprint sensor 700 may include a processor and/or memory for performing certain operations and this processor and/or memory may be utilized instead of or in addition to the depicted processor 720 and memory 730.

Ultrasonic sensor module 710, in some embodiments, be may be integrated as a portion of sensor processing unit 715. Any suitable ultrasonic sensing technology may be utilized in ultrasonic sensor module 710. For example, in some embodiments, an array of ultrasonic transducers (e.g., PMUT devices such as PMUT 601 in an array such as array 600) may be utilized. However, other types of ultrasonic sensors and/or arrays thereof may be utilized.

In one embodiment, fingerprint sensor 700 includes processor 720 for performing the pixel capture, where pixel capture is performed using subsets of ultrasonic transducers (e.g., PMUTs) of fingerprint sensor 700 operating under instruction from processor 720. In this manner, fingerprint sensor 700 can ultrasonically capture an image of a fingerprint (referred to herein as "capturing a fingerprint"). In other embodiments, processor 720 can perform at least some signal analysis, e.g., thresholding, to determine whether an object has interacted with fingerprint sensor 700. In other embodiments, processor 720 can analyze captured pixels and determine whether the object has characteristics of finger, e.g., a pattern resembling the ridge/valley pattern of a fingerprint. In other embodiments, fingerprint sensor 700 can capture a fingerprint and processor 720 can forward it to a processor (e.g., a host processor) of system circuitry or elsewhere for further analysis. In some embodiments, processor 720 can analyze a captured fingerprint by comparing its data to the data of a fingerprint stored in memory 730 and authenticate the captured fingerprint when it determines there is match between the captured and stored fingerprints. In some embodiments, fingerprint sensor 700 also determines the presence, and in some embodiments the positioning, of a finger relative to sensor(s) of ultrasonic sensor module 710 which are utilized to capture a fingerprint.

In various embodiments, fingerprint sensor 700 can include ultrasonic transducers (e.g., PMUTs in some embodiments) able to generate and detect acoustic/pressure waves. Examples of PMUT devices and arrays of PMUT devices are described in accordance with FIGS. 1A-6 above. However, fingerprint sensor 700 may utilize other types of ultrasonic sensors besides PMUTs. In embodiments, a medical device includes fingerprint sensor 700 comprised of an array of ultrasonic transducers that can facilitate ultrasonic signal generation and sensing. For example, fingerprint sensor 700 can include a silicon wafer having a two-dimensional (or one-dimensional) array of ultrasonic transducers.

Figure 7B:
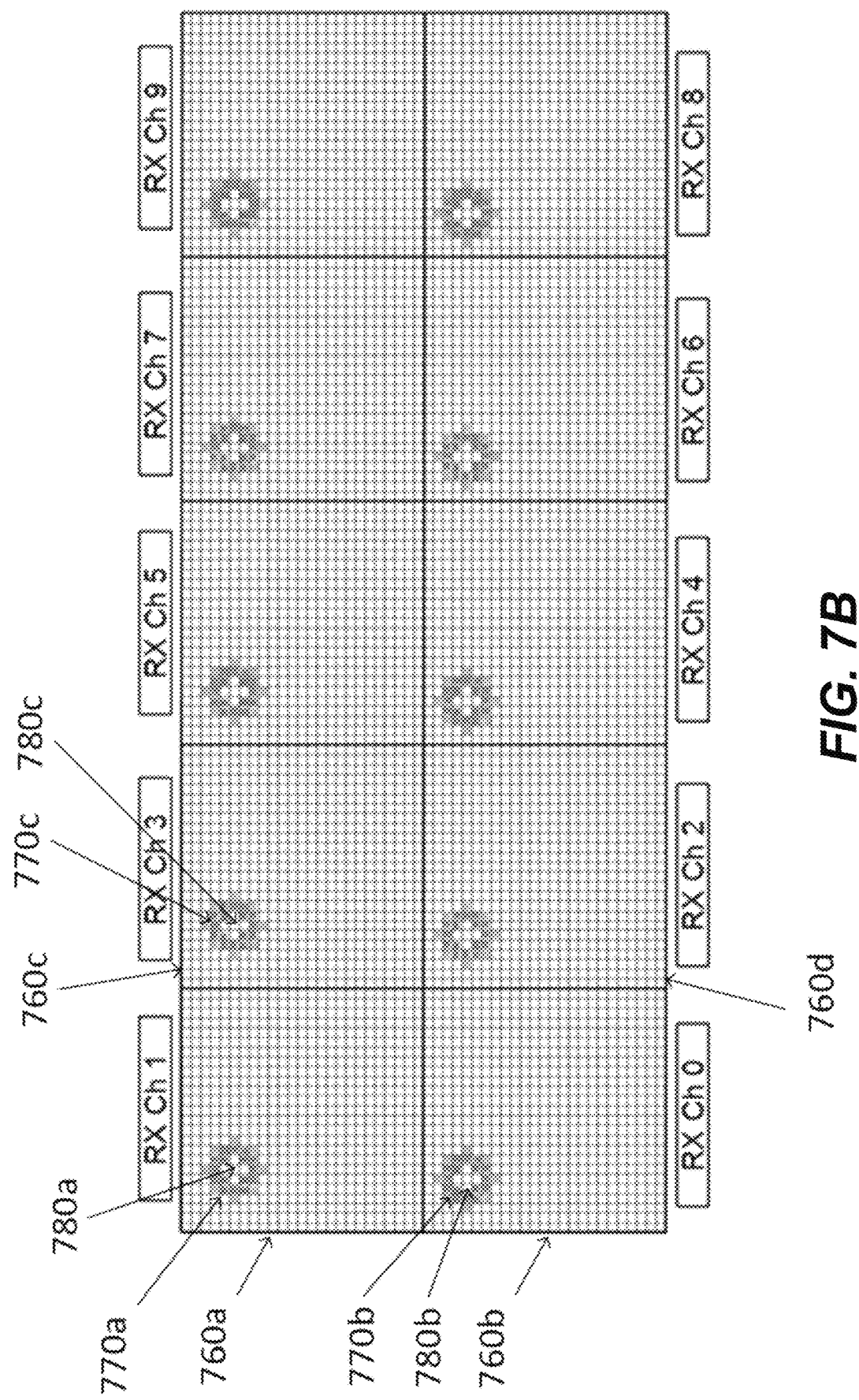
FIG. 7B illustrates example concurrent operation of pixel capture for a multiple array positions in a two-dimensional array of ultrasonic transducers, according to some embodiments.

FIG. 7B illustrates example concurrent operation of pixel capture for a multiple array positions in a two-dimensional array 711 of ultrasonic transducers, according to some embodiments. Array 711 is similar to array 600, but larger. In some embodiments, an ultrasonic sensor array similar to array 711 comprises the ultrasonic sensors of ultrasonic sensor module 710. A beamforming pattern is defined for two-dimensional array 711. In the illustrated example, two-dimensional array 711 is 50×125 ultrasonic transducers, separated into ten identical 25×25 segments 760 (four of which are illustrated as sub-blocks 760a-d). It should be appreciated that embodiments are not limited to this array size. When a sequence of activation to generate an ultrasound beam and sensing reflected echoes is completed under direction of processor 720, the beamforming pattern (e.g., beamforming patterns 770a, 770b, and 770c) is moved according to a pixel capture sequence (e.g., rightward or leftward, or upward and downward), with respect to the two-dimensional array 711 of ultrasonic transducers, and the sequence is repeated until all (or a specified amount) of pixels have been imaged. As the beamforming pattern moves, so does the receive pattern of ultrasonic transducers activated during a receive operation (e.g., receive patterns 780a, 780b, and 780c).

It should be appreciated that any type of pixel capture sequence may be used (e.g., side-to-side, top-to-bottom, random, another predetermined order, row and/or column skipping, etc.) by processor 720. Moreover, it should be appreciated that FIG. 7B illustrates a phase delay pattern that is symmetric about a focal point of the transmitting pixels. Once a beamforming space has been defined to designate which ultrasonic transducers in the beamforming space will be used for transmission of ultrasonic signals (e.g., the beamforming pattern), for receipt of reflected ultrasonic signals (e.g., the receive pattern), or for nothing (remain inactive), the ultrasonic sensor programs the transmit beamforming pattern and receive beamforming pattern into at least one location within the ultrasonic transducer array.

In one embodiment, an array controller (e.g., an array engine, array control logic, or processor 720) and array control shift register logic of the ultrasonic sensor programs this transmit beamforming pattern and receive pattern onto a plurality of locations within the ultrasonic transducer array. For example, with reference to FIG. 7B, the beamforming pattern is programmed at corresponding locations within each of the ten ultrasonic array sub-blocks so that up to ten image pixels can be captured in each transmit/received (TX/RX) operation, one pixel from each of the ten ultrasonic array sub-blocks. Imaging over the entire sensor area is then accomplished by stepping the beamforming patterns over the entire ultrasonic transducer array, transmitting and receiving at each step to capture a corresponding image pixel, where each sub-block corresponds to a segment of the image.

Section Three: Medical Devices with Integrated Ultrasonic Authentication

Figure 8A:
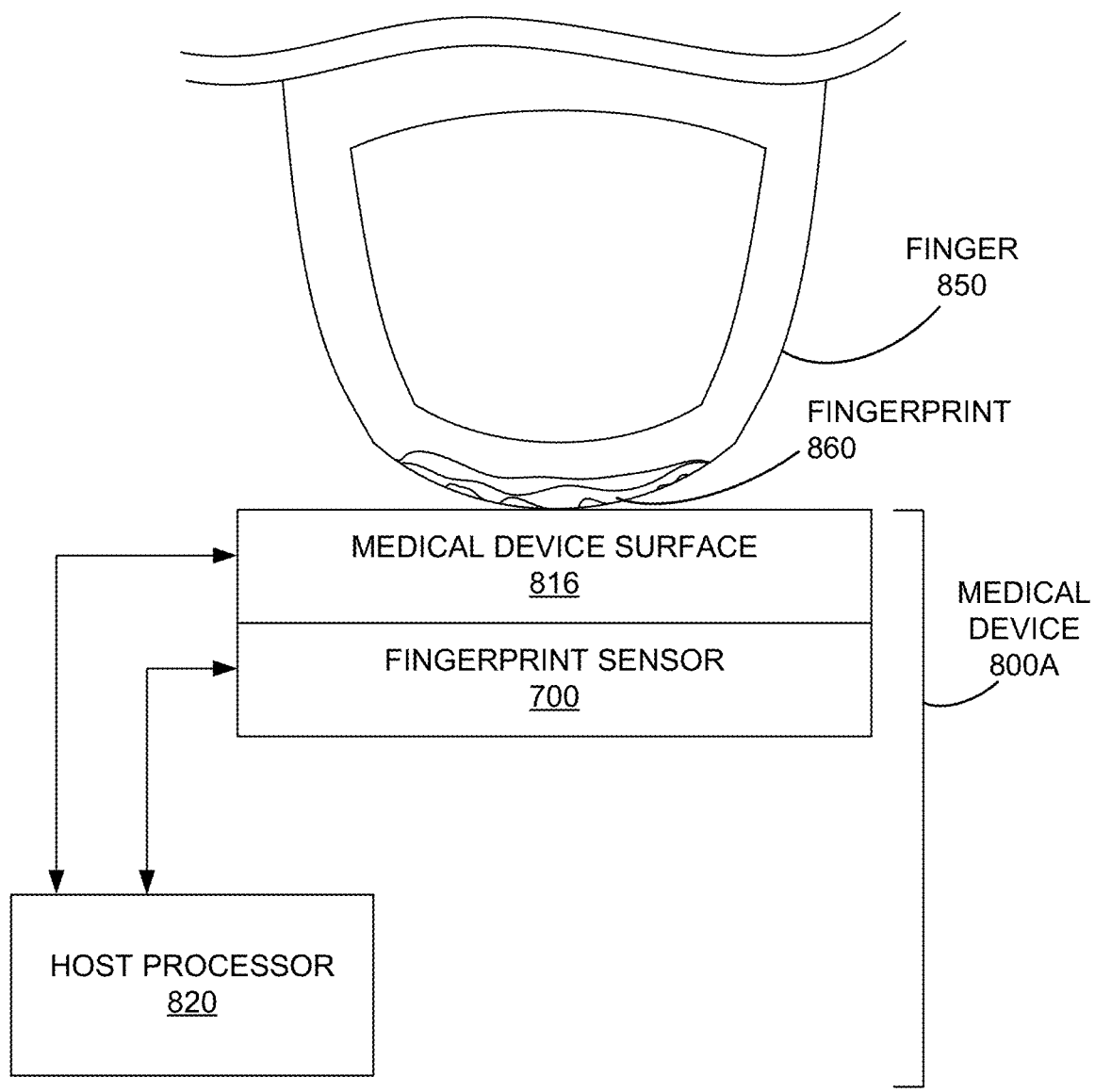
FIG. 8A illustrates an example medical device with an ultrasonic fingerprint sensor disposed beneath a surface of the medical device, according to various embodiments.

FIG. 8A illustrates an example medical device 800A with an ultrasonic fingerprint sensor 700 disposed beneath a surface 816 of the medical device, according to various embodiments. In general, the term "medical device" as used herein may be any device which comes into contact with the skin of a patient to measure a biological, physiological, and/or electrical attribute of the patient. A medical device, as described herein, comprises an ultrasonic sensor which captures a biometric reading such as a fingerprint, toeprint, skin print, arterial print, or the like from the skin of a patient. The captured biometric reading may be used to identify the patient, may be associated with measurements captured by the medical device, may be used to determine if the patient is authorized to operate the medical device, and/or may be used to activate operation of the medical device. Some examples of a "medical device" as described herein include, but are not limited to: an electroencephalograph, an electrocardiograph, a heartrate monitor, a plethysmograph, a sphygmomanometer, a blood glucose meter/tester, a bioelectrical impedance analysis body fat meter, and a digital weight measuring scale.

Medical device surface 816 is configured to interact with and/or contact skin of a patient during operation of medical device 800A. In some embodiments, medical device surface 816 may be or may include an electrode which can measure the pulse, the skin resistivity, or other aspect of a patient when the finger 850 of the patient is in contact with medical device surface 816. In various embodiments, medical device surface 816 may be a conductive surface, such as a metal surface or a conductive electrode. In some embodiments, the medical device surface 816 may be made of aluminum, stainless steel, or other conductive metal. As illustrated, medical device surface 816 may be coupled with a processor, such as host processor 820 and/or other electronics of medical device 800A which operate to capture a measurement from medical device surface 816. In some embodiments, a change in conductivity, pressure, resistivity, capacitance, the ground plane, or other electrically measurable property of medical device surface 816 may be used to detect that a finger, such as finger 850, is in contact with medical device surface 816. In some embodiments, the contact between the finger and the medical device surface is determined using the ultrasonic fingerprint sensor 700.

Fingerprint sensor 700 is an ultrasonic sensor disposed proximate, and in this example beneath, medical device surface 816 and configured to ultrasonically measure data with respect to a region above medical device surface 816. Ultrasonic signals pass back and forth through medical device surface 816, which may be a multi-layer stack of materials or a more complicated structure or may even be a single layer. In some embodiments, for example, medical device surface 816 is a metal electrode disposed atop fingerprint sensor 700. Using the ultrasonic fingerprint sensor 700, an ultrasonic image may be captured of an object or portion thereof that is above medical device surface 816. With reference to FIG. 1A, medical device surface 816 may be a platen layer, such as platen layer 116, above acoustic coupling layer 114 of the ultrasonic sensor module 710 used in fingerprint sensor 700. In other embodiments, medical device surface 816 may be coupled with or disposed above an existing platen layer of the array of ultrasonic sensor module 710 used in fingerprint sensor 700. In some embodiments, medical device surface may also be adjacent to fingerprint sensor 700 (e.g., abutting or within a couple centimeters) rather than situated above it. In some embodiments, fingerprint sensor 700 is an always-on device which is on and continuously operating anytime medical device 800A is powered on.

As will be discussed, fingerprint sensor 700 may detect and/or capture a fingerprint, such as fingerprint 860, of a finger 850 which contacts the medical device surface 816 below which fingerprint sensor 700 is disposed. In some embodiments, when such contact is detected, ultrasonic fingerprint sensor 700 may be activated. In some embodiments, ultrasonic fingerprint sensor 700 may operated to detect a finger and/or the position of a finger, such as finger 850, in contact with medical device surface 816.

In some embodiments, an ultrasonically captured image of fingerprint 860 may be authenticated by processor 720, such as by comparing data of the image of fingerprint 860 with data of one or more fingerprint images stored in a memory, such as memory 730. In some embodiments, an ultrasonically imaged/captured fingerprint 860 may be provided for similar authentication to another entity such as processor 820 or an entity external to medical device 800A. In some embodiments, data of a captured fingerprint image (or a name or identifier of a person with whom the fingerprint 860 is authenticated to be associated) may be associated with the operation of the medical device 800A after it is activated and/or with a measurement captured by medical device 800A after it is activated. For example, a pulse measurement, an EKG measurement, a glucose measurement, a heartrate, an oxygen saturation, or other medical measurement may be associated with an ultrasonically captured image of fingerprint 860 (whether or not the image of fingerprint 860 has been authenticated) or with the person to whom the fingerprint 860 is authenticated to belong.

In some embodiments a medical device, such as medical device 800A, may have more than one medical device surface which human skin contacts to facilitate capture of a medical measurement by the medical device. In such embodiments, an ultrasonic fingerprint sensor 700 may be disposed beneath one, some, or all of the medical device surfaces which human skin contacts for measurement purposes.

Because medical device electrodes for EEG, EKG, heartrate/pulse measurement, and the like use low-frequency electrical signals and the ultrasonic transducers of ultrasonic sensor module 710 uses high-frequency acoustic signals, the electrical and ultrasonic sensing typically do not interfere with one another. This allows the ultrasonic sensing to take place not only before electrical medical sensing, but during (i.e., simultaneous to) the electrical medical sensing of an EKG, EEG, heartrate/pulse measurement device, or the like without causing interference. In some embodiments, if there is concern of interference between ultrasonic and electrical sensing, filtering in either the ultrasound sensor device or the medical device may be employed to remove signal contributions of the other device. This simultaneous operation can be used to ensure that a finger has not moved (e.g., slipped, wiggled around, etc.) enough to depart from a desired sensing position. In some instances, an alarm or notification may be presented to a patient if positioning is not adequate. This simultaneous operation can be used to ensure that a finger maintains a proper amount of contact area (e.g., not too much or too little) to perform medical measurement. In some instances, an alarm or notification may be presented to a patient if contact is not adequate. This simultaneous operation continuously can also be used to ensure against fraud or spoofing of obtained medical measurements by validating that one person does not activate a device and then substitute another person from whom the medical measurement is acquired.

As previously described in conjunction with FIG. 7A, a processor is coupled with the ultrasonic sensor module 710 of fingerprint sensor 700. The processor may be a sensor processor, such as processor 720, which is integrated with ultrasonic fingerprint sensor 700 or another processor such as the host processor 820 of the medical device. In some embodiments, in response to detection of a finger (e.g., finger 850) in contact with medical device surface 816, the processor operates the ultrasonic sensor to capture a fingerprint (e.g., an ultrasonic image of fingerprint 860) of the finger. The captured fingerprint may be authenticated by the processor or forwarded elsewhere external to the processor for authentication. The external location may be external to fingerprint sensor 700 but within medical device 800A or may be external to medical device 800A. By "authentication" what is meant is that a determination is made that the captured fingerprint is associated with (i.e., belongs to) a person who is authorized to use medical device 800A. In some embodiments the authentication may include identifying the person (such as by name or patient number). For example, the processor may provide the captured fingerprint for authentication by an entity external to the processor; and then receive, from the entity external to the processor, either an authentication that the person associated with the captured fingerprint is authorized to use medical device 800A or a message that the captured fingerprint is unauthenticated (i.e., not associated with a person authorized to use medical device 800A). In response to authentication, by whatever means, that a person associated with the captured fingerprint is authorized to use the medical device, the processor activates operation of the medical device 800A such as by sending a signal to processor 820 and/or other circuitry of medical device 800A that allows the collection of medical data to begin.

In some embodiments, once a patient/user of medical device 800A is authenticated information such as the captured fingerprint data or an identification number of the patient is added to or associated with the medical data measured by medical device 800A while activated. In some embodiments, if a user/patient is not authenticated the medical device 800A may still be activated and any medical measurements collected by medical device 800A during this activation are marked as "not authenticated" and/or are appended with the non-authenticated captured fingerprint.

Figure 8B:
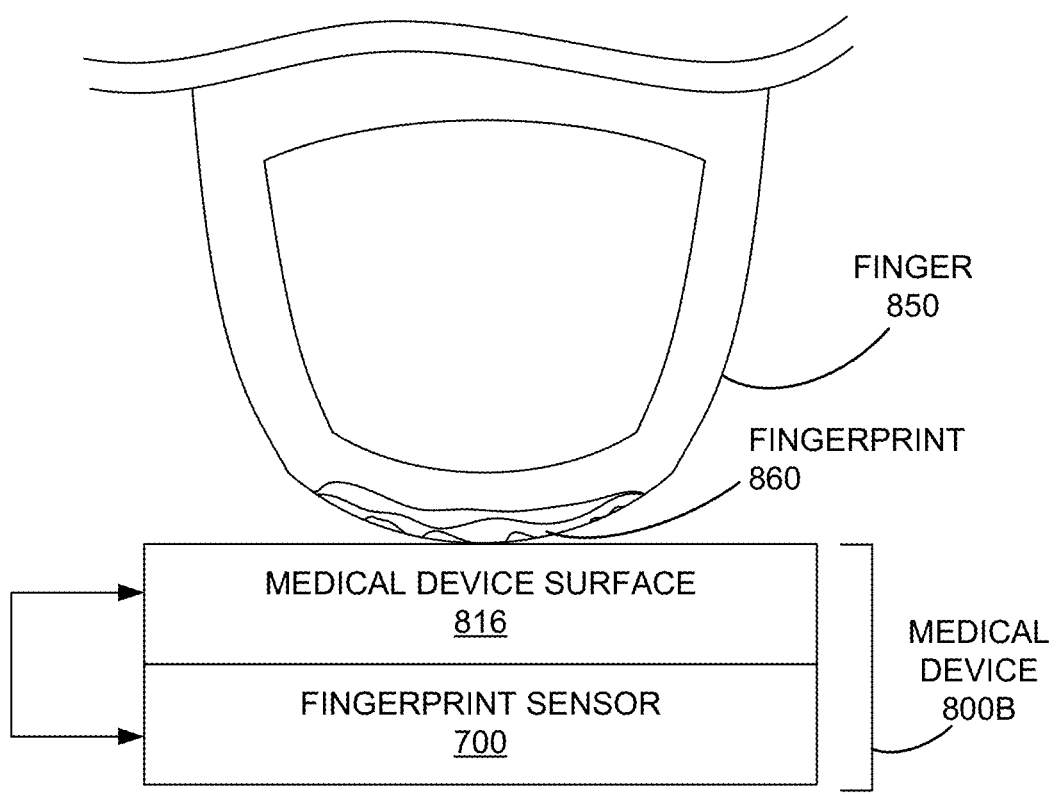
FIG. 8B illustrates an example medical device with an ultrasonic fingerprint sensor disposed beneath a surface of the medical device, according to various embodiments.

FIG. 8B illustrates an example medical device 800B with an ultrasonic fingerprint sensor 700 disposed beneath a surface 816 of the medical device, according to various embodiments. FIG. 8A differs from FIG. 8B in that medical device 800B does not have host processor 820 which is depicted in medical device 800A and instead relies upon processor 720 of fingerprint sensor 700. That is, in medical device 800B processor 720 of sensor processing unit 715 performs any processing of acquired medical measurements. In some embodiments, for example, processor 720 may include extra pins for I/O of medical signals. Additionally, processor 720, operates (if required) to communicate acquired medical measurements to an entity remotely located from medical device 800B, performs any local processing of fingerprints which are ultrasonically captured (which may include authenticating them against stored fingerprint data), communicates with an entity external to medical device 800B regarding captured fingerprints if required, and/or authorizes activation of medical device 800B to capture medical measurements from a patient. Performing the medical data acquisition/processing and the fingerprint capture in the same processor increases performance and provides easier, more streamlined fusion of the medical and fingerprint data. It also is more secure and reduce changes of fraud.

Figure 9:
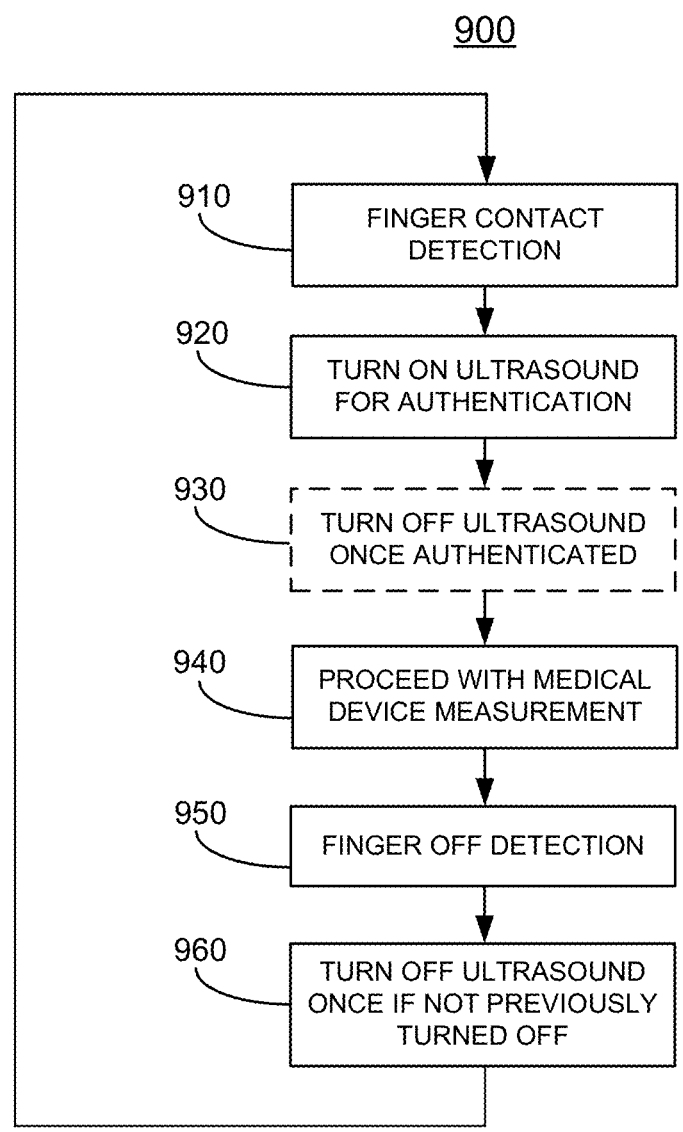
FIG. 9 illustrates a flow diagram of an example method of implementing authentication when measuring with a medical device, according various embodiments.

FIG. 9 illustrates a flow diagram 900 of an example method of implementing authentication when measuring with a medical device, according various embodiments. Reference will be made to notional medical device 800 (which may be either of medical devices 800A or 800B) in discussing procedures of flow diagram 900, however it should be realized that the procedures may be implemented with other medical devices.

At 910 of flow diagram 900, in one embodiment, finger contact of a finger 850 is detected on a surface 816 of medical device 800. This contact may be detected by the ultrasonic fingerprint sensor 700 or by electrical sensors, capacitive sensors, pressure sensors, force sensors, or other sensors coupled with medical device surface 816.

At 920 of flow diagram 900, in one embodiment, in response to detecting finger contact, ultrasonic fingerprint sensor 700 is turned on to detect the location and/or capture fingerprint 860 of the finger 850. An ultrasonically captured fingerprint 860 (i.e., an image of fingerprint 860) is authenticated or sent for authentication. Many contact characteristics, such as the position of the finger, the amount of contact surface of the finger, and the contact pressure of the finger may all be determined by fingerprint sensor 700 from an image of a captured fingerprint. Another example of a contact characteristic is which finger the user is putting above the sensor on the medical device surface 816. These contact characteristics or contact parameters can be monitored by fingerprint sensor 700. For one or more of these characteristics/parameters and/or to store a fingerprint for authentication a calibration procedure may be required. The calibration may comprise e.g., fingerprint/user enrollment process which involves capturing and storing a fingerprint image of an authorized user/patient. The calibration may comprise determining the best finger for a medical measurement and/or determining the best position and/or pressure of a finger for the medical measurement, for example, with respect to features or structures of the finger such as e.g., blood vessels. Based on the contact characteristic(s) a confidence factor of the medical measurement may be determined to rate the likelihood that a valid measurement can be obtained. The confidence factor may numerically express a level of confidence that the contact characteristic will facilitate successful measurement and collection of medical data with the medical device (e.g., that positioning is proper for measurement, that movement does not exceed a threshold needed for successful measurement, that contact area is sufficient for measurement, that contact pressure is sufficient measurement, etc.). The confidence factor may be a percentage, may be normalized to predetermined scale, or may take another numerical form. The contact characteristics may be monitored continuously during the medical measurement and the confidence factor may be also determined continuously and stored with the medical data (stream).

At 930 of flow diagram 900, in one embodiment, after the captured fingerprint has been authenticated by whatever means, the ultrasonic fingerprint sensor 700 may be turned off or switched to a different mode. In some embodiments, this procedure is optional and the ultrasonic fingerprint sensor 700 may be left on throughout activation of medical device 800 or for a longer period of time, such as to monitor movement, contact, or to provide repeated authentication of a patient.

At 940 of flow diagram 900, in one embodiment, medical device 800 is activated and proceeds with measurements performed by the medical device. Data collected from medical measurements may be stored locally (e.g., in memory 730 or other local storage) and/or may be communicated to an entity external to medical device 800. In some embodiments, medical device 800 may be activated upon a positive authentication of a captured fingerprint. In some embodiments, the confidence factor may be used with the authentication to activate operation of medical device 800. For example, medical device 800 may only be activated to collect a medical measurement when the contact characteristic has a confidence above a predetermined threshold and the authentication is also successful. In some embodiments, when authentication is not important or required, medical device 800 may be activated to collect a medical measurement when the contact characteristic has a confidence above a predetermined threshold.

At 950 of flow diagram 900, in one embodiment, when a finger is detected as being off the sensor, the medical device is turned off/deactivated, medical measurements cease, and detection for presence of a finger in contact with medical device 800 may begin again while medical device 800 is powered on. The finger off detection may be performed by the ultrasonic fingerprint sensor 700 or by electrical sensors, capacitive sensors, pressure sensors, or other sensors coupled with medical device surface 816.

At 960 of flow diagram 900, in one embodiment, the ultrasound from the ultrasonic fingerprint sensor 700 is turned off if it has not previously been turned off at 930.

Figure 10A:
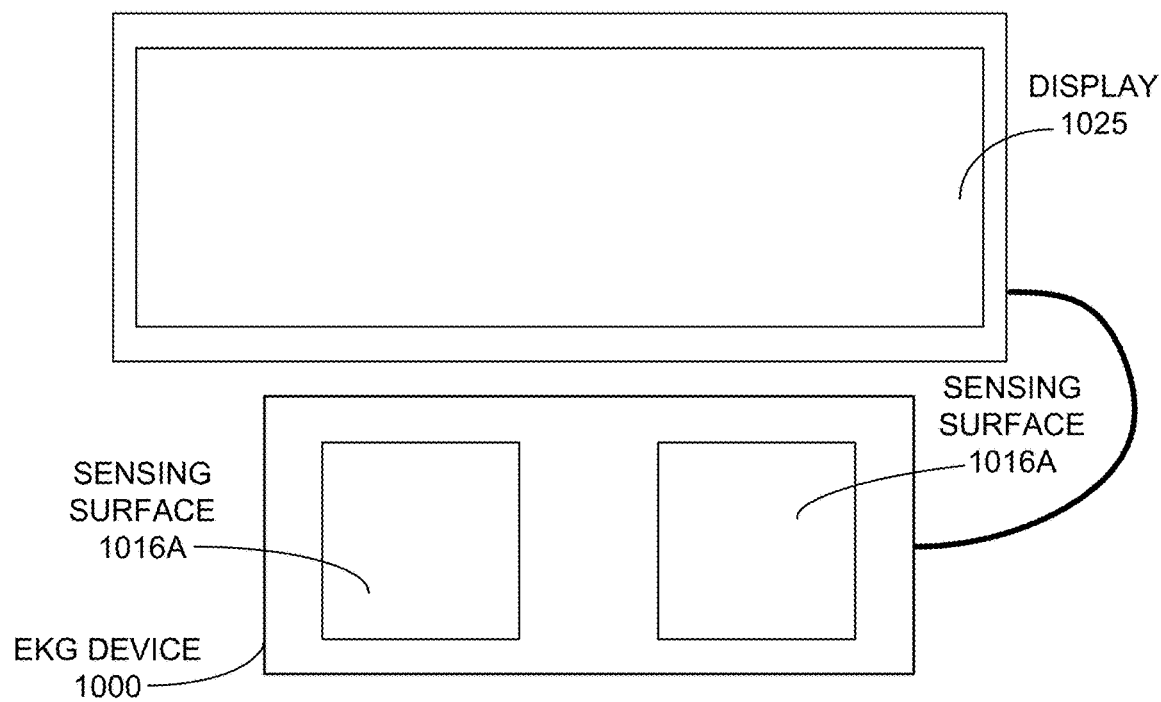
FIGS. 10A and 10B illustrate an example portable electrocardiogram (EKG) medical device with an ultrasonic fingerprint sensor disposed beneath a surface of the medical device, according to various embodiments.

FIG. 10A illustrates an example portable electrocardiogram (EKG) medical device 1000 with an ultrasonic fingerprint sensor (not visible) disposed beneath a surface of the medical device, according to various embodiments. For example, in the manner depicted in FIGS. 8A and 8B, an ultrasonic fingerprint sensor 700 may be disposed beneath one or both of sensing surface 1016A and sensing surface 1016B. As depicted, in some embodiments, EKG medical device 1000 may include or be communicatively coupled with a display 1025. The display may be a display screen of a smartphone or a tablet computing device in some embodiments.

Figure 10B:
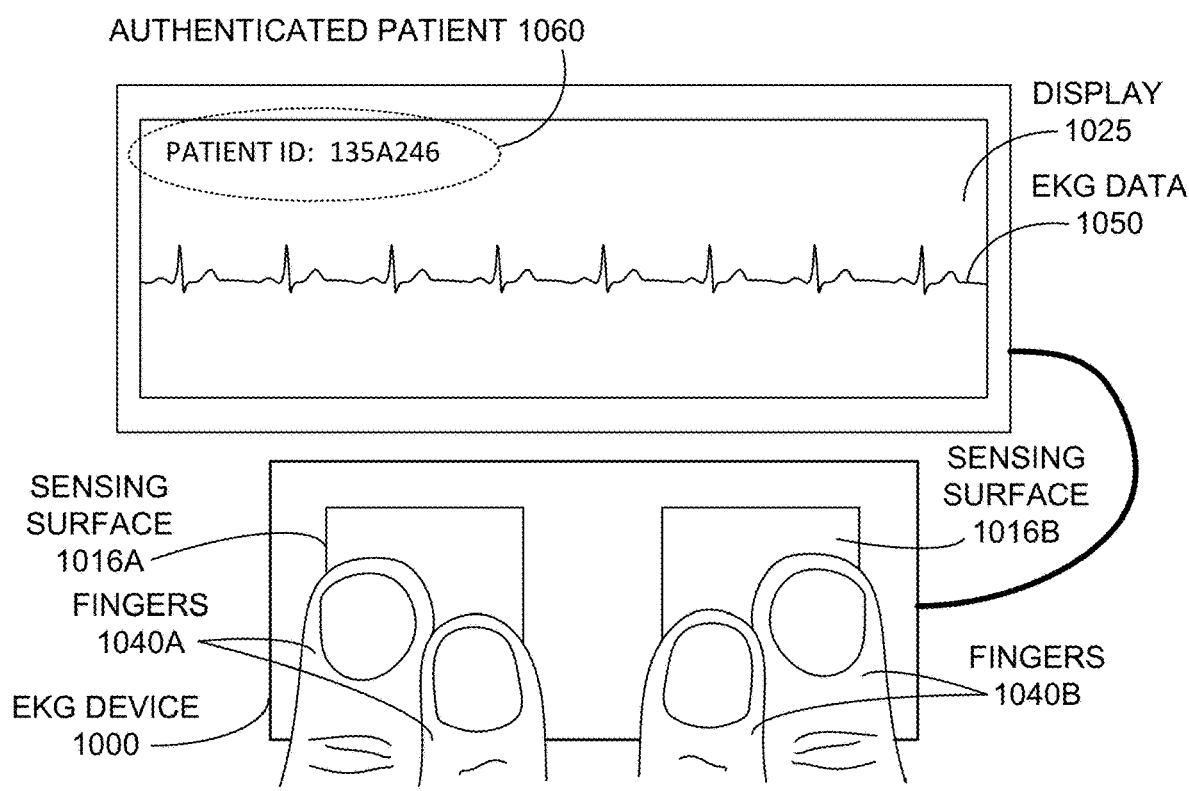

FIG. 10B illustrates the portable EKG medical device 1000 of FIG. 10A in use, where one or more fingers 1040A from a user's left hand are contacting sensing surface 1016A and one or more fingers 1040B from a user's right hand are contacting sensing surface 1016B. In one embodiment, a fingerprint sensor disposed beneath one or both of sensing surface 1016A and 1016B has captured a fingerprint of one or more of fingers 1040A and 1040B, and that fingerprint has been authenticated as belonging to an authenticated patient 1060 with patient ID number 135A246. In response to the authentication, an EKG data 1050 is measured by the sensing surfaces 1016A and 1016B. The EKG data 1050 is displayed on display 1025 and is associated with authenticated patient 1060. The EKG data may similarly be stored or transmitted in association with the authenticated patient 1060.

Figure 11:
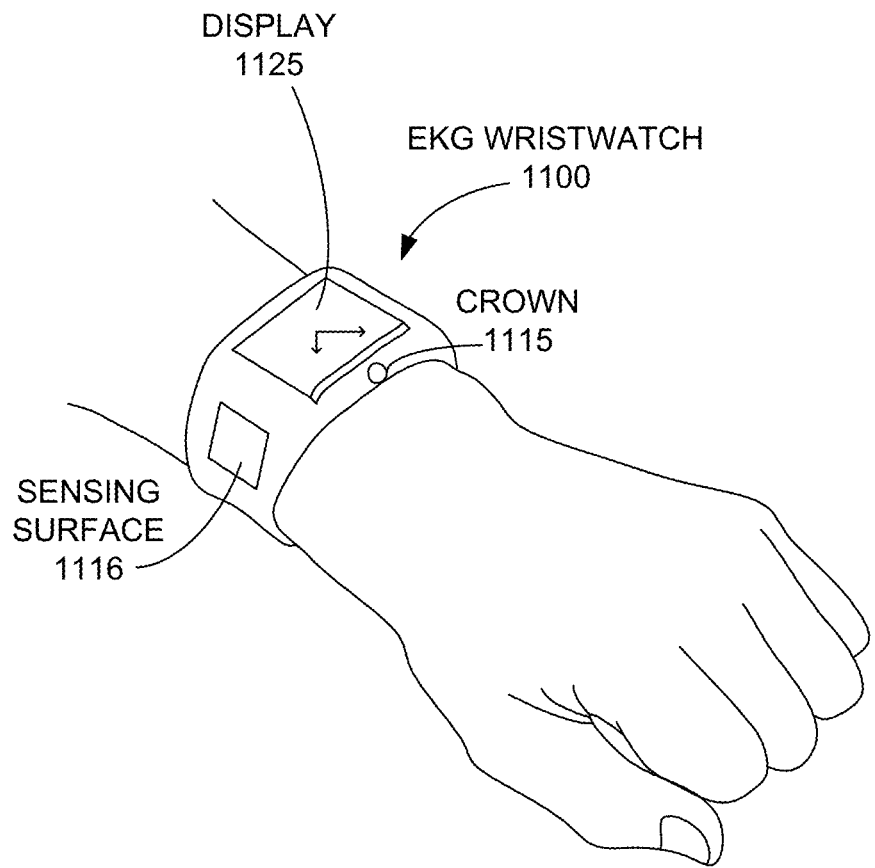
FIG. 11 illustrates an example wearable EKG wristwatch medical device with an ultrasonic fingerprint sensor disposed beneath a surface of the medical device, according to various embodiments.

FIG. 11 illustrates an example wearable EKG wristwatch medical device 1100 with an ultrasonic fingerprint sensor (not visible) disposed beneath a surface of the medical device, according to various embodiments. For example, in the manner depicted in FIGS. 8A and 8B, a fingerprint sensor 700 may be disposed sensing surface 1116. In other embodiments, a fingerprint sensor 700 may alternatively or additionally be disposed beneath another surface such as crown 1115. A user may touch sensing surface 1116 or crown 1115 with one or more fingers from their right hand while wearing EKG wristwatch medical device 1100 on their left hand. In some embodiments a second sensor electrode may be disposed beneath display 1125 such that it contacts the skin of the wearer's left wrist. A second electrode may be disposed in other locations, such as part of the surface of crown 1115. User authentication and operation of medical device 1100 is similar to what is described in FIG. 10B.

Figure 12:
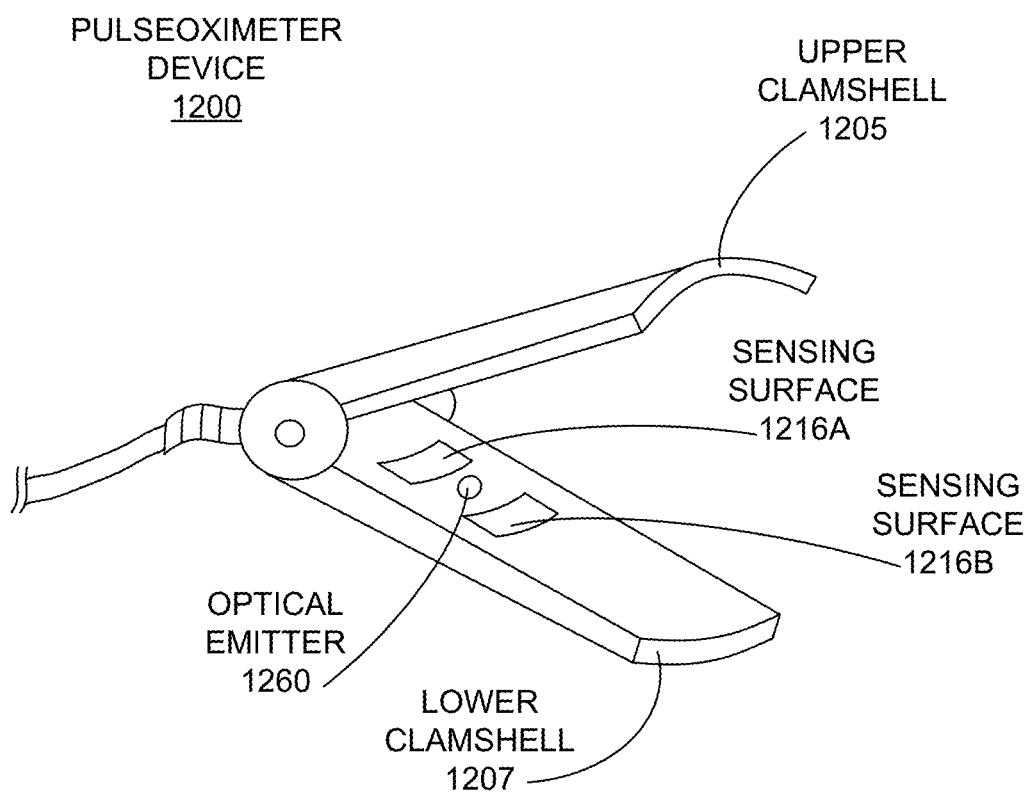
FIG. 12 illustrates an example pulse oximeter medical device with an ultrasonic fingerprint sensor disposed beneath a surface of the medical device, according to various embodiments.

FIG. 12 illustrates an example pulse oximeter medical device 1200, also known as a photoplethysmograph or PPG, with an ultrasonic fingerprint sensor (not visible) disposed beneath a surface of the medical device, according to various embodiments. Pulse oximeter medical device 1200 may include one or both of sensing surfaces 1216A and 1216B on lower clamshell 1207. For example, in the manner depicted in FIGS. 8A and 8B, an ultrasonic fingerprint sensor 700 may be disposed beneath one or both of sensing surface 1216A and sensing surface 1216B. Also, included on lower clamshell 1207 is an optical emitter 1260. Not visible is an optical receiver disposed in upper clamshell 1205. In operation, the finger of a patient (e.g., finger 850) is inserted between upper clamshell 1205 and lower clamshell 1207 and then the clamshells are closed around the finger. Optical emitter 1260 emits a light which shines through the finger and is received by the optical receiver and used to measure oxygen saturation in the blood of the finger. The pulse oximeter may measure both the pulse and the oxygen saturation of a patient. Use of sensing surfaces 1216A and 1216B along with ultrasonic fingerprint sensors disposed beneath one or both, assists in ensuring that the finger of a patient is present and properly positioned (i.e., a portion of a fingerprint can be detected and captured above each sensing surface 1216A and 125B). Additionally, or alternatively, when a fingerprint is captured and/or authenticated pulse oximeter medical device 1200 can be activated to measure pulse and oxygen saturation. The captured/authenticated fingerprint (or person to which it is authenticated) can be associated with the operation of medical device 1200 and the medical measurements captured by medical device 1200.

Figure 13A:
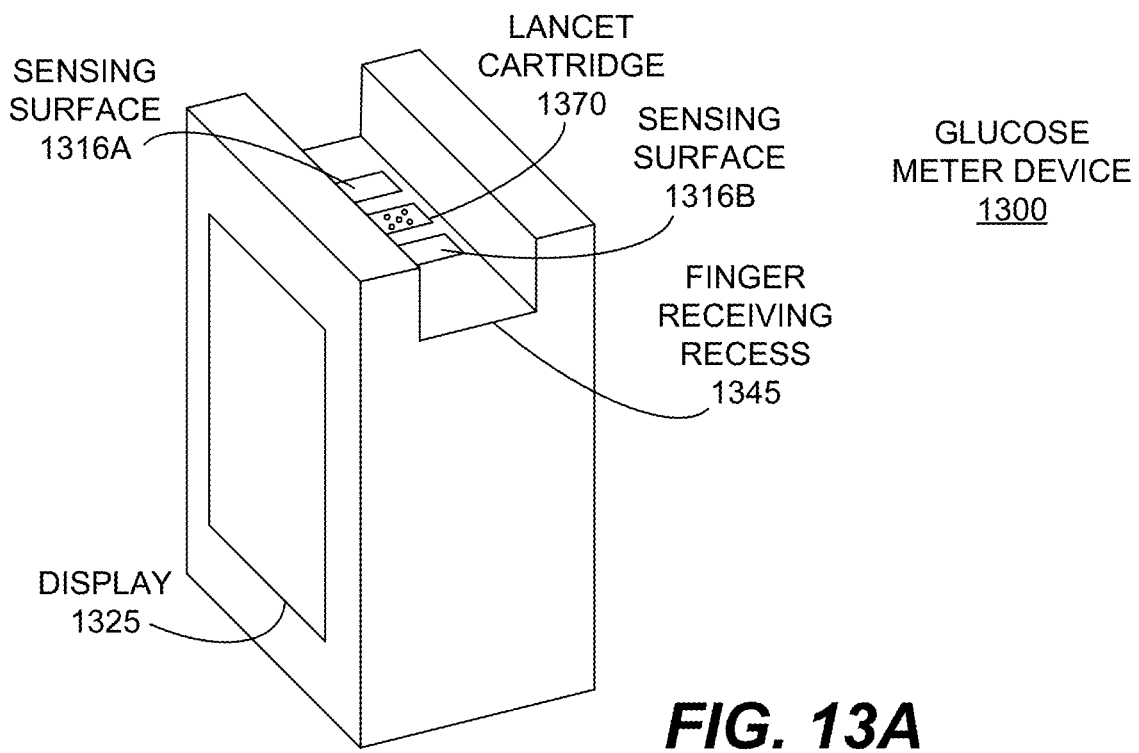
FIGS. 13A and 13B illustrate an example blood glucose meter medical device with an ultrasonic fingerprint sensor disposed beneath a surface of the medical device, according to various embodiments.

FIG. 13A illustrates an example portable blood glucose meter medical device 1300 with an ultrasonic fingerprint sensor disposed beneath a surface of the medical device, according to various embodiments. As with a conventional needle stick device a lancet is utilized to prick a finger of a patient to capture a blood sample for analysis. In the depicted embodiment, a cartridge 1370 of single use lancets is disposed in a finger receiving recess 1345 proximate to at least one sensing surface 1316 (in this embodiment, between sensing surface 1316A and sensing surface 1316B).

Blood glucose meter medical device 1300 may include one or both of sensing surfaces 1316A and 1316B disposed within finger receiving recess 1345. For example, in the manner depicted in FIGS. 8A and 8B, an ultrasonic fingerprint sensor 700 may be disposed beneath one or both of sensing surface 1316A and sensing surface 1316B. In some embodiments the sensing surfaces 1316A and 1316B may be the external surfaces of ultrasonic sensors. In some embodiments, an ultrasonic fingerprint sensor may be configured into the surface of lancet cartridge 1370. It should also be appreciated that the shape of blood glucose meter medical device 1300 and its finger receiving recess 1345 are merely example, and that other shapes and configurations are possible and anticipated.

Figure 13B:
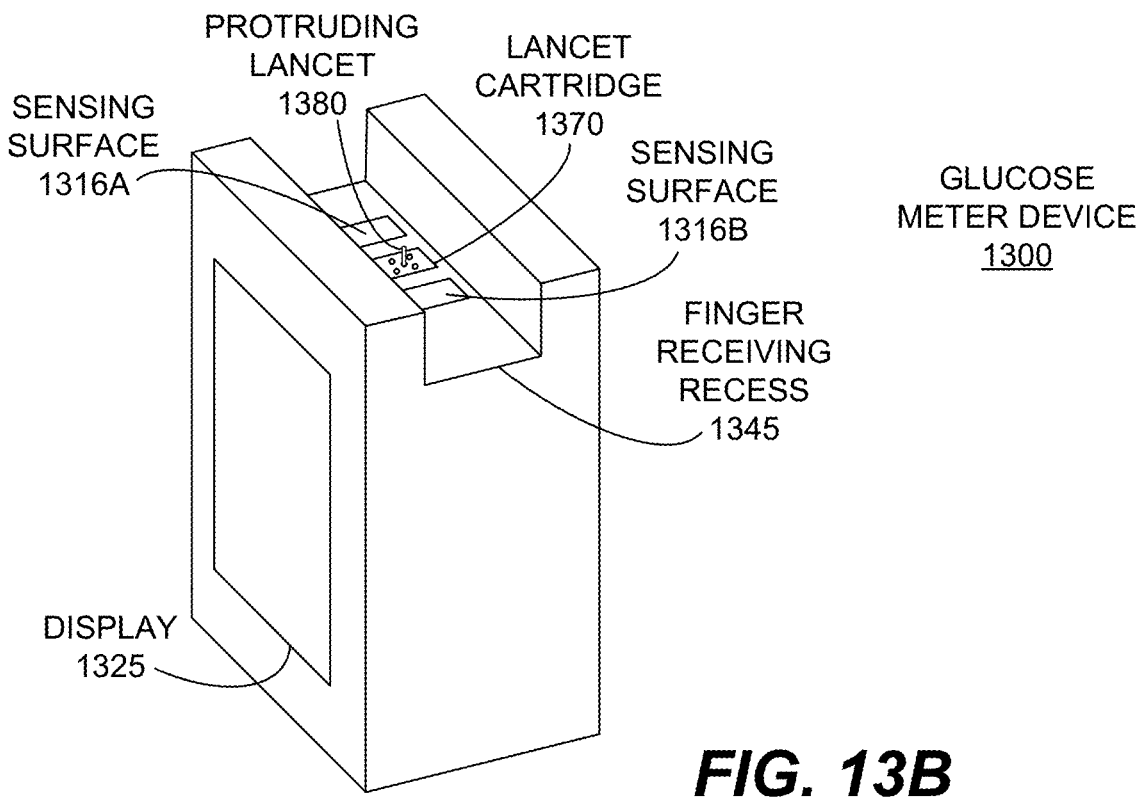

FIG. 13B illustrates the example blood glucose meter medical device 1300 of FIG. 13A with a single use needle/lancet 1380 protruding from lancet cartridge 1370. Typically, the lancet 1380 will protrude into the tip of a finger such as finger 850. The finger is not depicted in FIG. 13B, as it would obscure visibility of the protruding lancet 1380. Use of sensing surfaces 1316A and/or 1316B along with ultrasonic fingerprint sensors disposed beneath one or both, assists in ensuring that the finger of a patient is present and properly positioned (i.e., a portion of a fingerprint can be detected and captured above one or both sensing surfaces 1316A and 1316B). In some embodiments, when a finger is properly positioned a needle or lancet of lancet cartridge 1370 is triggered to protrude out of the blood glucose meter medical device 1300 and into the finger which is positioned in finger receiving recess 1345. Additionally, or alternatively, when a fingerprint is captured and/or authenticated blood glucose meter medical device 1300 can be activated such that a needle or lancet of lancet cartridge 1370 is triggered to protrude out of blood glucose meter medical device 1300 and into finger which is positioned in finger receiving recess 1345. In this manner the presence and location of a patient's finger can be detected with high confidence, thus making blood glucose meter medical device 1300 safer to use and less prone to false/improper activation. Blood glucose can be measured from a blood sample obtained by the lancet/needle and the results displayed on display, such as display 1325, which may be integrated with glucose meter medical device 1300. In some embodiments, the captured/authenticated fingerprint (or person to which it is authenticated) is associated with the operation of blood glucose meter medical device 1300 and the medical measurements captured by blood glucose meter medical device 1300.

Although depicted with the use of a lancet cartridge 1370, ultrasonic fingerprint sensing may similarly be employed with a single use disposable lancet which is positioned to collect a blood sample contemporaneously with capture of an image of the fingerprint from which a blood sample is acquired.

In some embodiments, a plurality of medical devices may be used. The plurality of medical devices may be grouped together or connected together in some form of network or cloud. The fingerprint identification may then be used to associate medical data from different devices with a single patient. For example, medical data having an associated fingerprint identifier can come from a plurality of medical devices and then be grouped together (i.e., associated with a single user/patient) based on the associated fingerprint identifier. The fingerprint identifier may be used without actually identifying the patient/user's name. It is only used to give a unique identifier based on the fingerprint, while the user stays anonymous. The fingerprint identifier may be the image of the captured fingerprint or maybe derived from the image of the captured fingerprint. Consider an example application where a user performs a series of tests using different medical devices, each equipped with a fingerprint sensor. Another example application may be a user using a series of sport equipment, each equipped with a medical device capable of measuring medical data, such as e.g., heart rate. The medical data and/or other data acquired while the user used the different sports equipment can be grouped together using the fingerprint identifier. Settings of the different devices may also be adapted based on the medical data acquired on previous devices or equipment, for example to determine the state of health and/or fatigue of the user.

Example Method(s) of Operation

FIGS. 14A-14F illustrate a flow diagram of an example method of operating a medical device, in accordance with various embodiments. Procedures of this method will be described with reference to elements and/or components of one or more of FIGS. 1A-13B. It is appreciated that in some embodiments, the procedures may be performed in a different order than described, that some of the described procedures may not be performed, and/or that one or more additional procedures to those described may be performed. Flow diagram 1400 includes some procedures that, in various embodiments, are carried out by one or more processors (e.g., sensor processor 720 of sensor processing unit 715 and/or host processor 820) under the control of computer-readable and computer-executable instructions that are stored on non-transitory computer-readable storage media (e.g., memory 730). When describing procedures of flow diagram 1400 reference will be made to components of medical device 800 (which may be either or both of medical devices 800A or 800B), however it should be borne in mind that the procedures may be similarly implemented with other medical devices, such as those described in FIGS. 10-13B. It is further appreciated that one or more procedures described in flow diagram 1400 may be implemented in hardware, or a combination of hardware with firmware and/or software. Additionally, it should be appreciated that the procedures are being described with respect to circuit boards and servers, however they may be implemented in other devices with cooling systems.

With reference to FIG. 14A, at procedure 1410 of flow diagram 1400, in various embodiments, a finger is detected in contact with a portion of the medical device. With reference to medical device 800, the portion may comprise medical device surface 816 and the contact may be detected by an ultrasonic fingerprint sensor 700 or by electrical sensors, capacitive sensors, pressure sensors, or other sensors coupled with medical device surface 816.

With continued reference to FIG. 14A, at procedure 1420 of flow diagram 1400, in various embodiments, responsive to detecting the finger, an ultrasonic sensor disposed beneath the portion of the medical device captures a fingerprint of the finger while the finger is in contact with the portion of the medical device. With reference to medical device 800, this may comprise ultrasonic fingerprint sensor 700 capturing an ultrasonic image of the fingerprint 860 of finger 850 while finger 850 contacts medical device surface 816.

The captured fingerprint may be authenticated by comparison to stored data of authenticated or registered users and finding a match. This authentication may be performed locally in medical device 800 by comparison to locally stored information. This authentication may additionally or alternatively be performed remotely by communicating data of the captured fingerprint to an entity, such as a hospital patient system and database, which is external to medical device 800. If no match is found, then fingerprint is unauthenticated.

With continued reference to FIG. 14A, at procedure 1430 of flow diagram 1400, in various embodiments, responsive to authenticating that a person associated with the captured fingerprint is authorized to use the medical device, operation of the medical device is activated. With reference to medical device 800 in FIGS. 8A and 8B, a processor, such as processor 720 or 820 may activate the operation of medical device 800.

In some embodiments, this comprises activating the operation of medical device 800 only for a duration of time that the finger 850 remains detected in contact with the portion (e.g., medical device surface 816) of medical device 800.

In some embodiments, this comprises activating the operation of medical device 800 upon verification that movement of the finger 850 is within a predetermined sufficient range of movement (such as having movement below a preset motion threshold) for the operation of medical device 800. A confidence factor and comparison to a threshold may be used to quantify and/or verify movement.

In some embodiments, this comprises activating the operation of medical device 800 upon verification that contact area of the finger 850 is sufficient for the operation of medical device 800 (e.g., the portion of fingerprint 860 detected/captured exceeds a predetermined area threshold and/or is within a desired area range). For example, this can be done be analyzing the portion or percentage of the ultrasonic image acquired by fingerprint sensor 700 that comprises a fingerprint image comprising a ridge/valley pattern. A confidence factor and comparison to a threshold may be used to quantify and/or verify contact area.

In some embodiments, this comprises activating the operation of medical device 800 upon verification that contact pressure of the finger 850 is sufficient for the operation of medical device 800 (e.g., the portion of fingerprint 860 detected/captured exceeds a predetermined contact pressure threshold and/or is within a desired contact pressure range). The pressure of the finger on medical device surface 816 may be derived based on the changes of the ridge/valley pattern as the user puts down the finger. For example, when the pressure increases the valleys get smaller and the ridges get wider. The derived pressure may be compared to a pressure threshold to determine if the user is pressing hard enough on the medical device surface 816. A confidence factor and comparison to a threshold may be used to quantify and/or verify contact pressure.

In some embodiments, this comprises activating the operation of medical device 800 upon verification that position of finger 850 is sufficient for the operation of medical device 800 (e.g., the portion of fingerprint 860 detected/captured is properly positioned within some margin of error to receive a stick from a lancet or to contact a sensor). A confidence factor and comparison to a threshold or stored exemplar may be used to quantify and/or verify position.

In some embodiments, this comprises activating a conductive sensor to capture electrical measurements from finger 850, where the conductive sensor is disposed between the finger 850 and the ultrasonic fingerprint sensor 700 at the portion (e.g., the conductive sensor may be medical device surface 816) of the medical device 800. In some embodiments, this comprises activating a photoplethysmography device to obtain measurements from the finger. In some embodiments, this comprises activating an EKG device to obtain measurements from the finger. In some embodiments, this comprises activating a needle stick measuring device (e.g., a lancet) to protrude out of the medical device and into the finger and/or comprises activating the analysis of a captured blood sample.

Although an image of a fingerprint is described as being captured for authentication before medical device 800 is activated, in some embodiments, an image of a fingerprint may be captured while medical data is being measured and/or after medical data has ceased being measured. Either or both instances of additional capture may be conducted to further authenticate and validate that the medical data is associated with a single person throughout the measurement. During the operation of the medical device, the fingerprint sensor may also be operated in a mode different than the identification mode, for example to reduce required computing resources or power resources or to perform other functions. In some embodiments, the mode may be optimized to determine the contact characteristics of the finger, such as e.g., position, contact area, pressure, etc.

With reference to FIG. 14B, at procedure 1440 of flow diagram 1400, in various embodiments, the method as illustrated in FIG. 14A further includes authenticating that the person associated with the captured fingerprint is authorized to use the medical device. In some embodiments, the authenticating may be performed by a processor, such as processor 720 or host processor 820 and may involve comparing data of a captured fingerprint to data of one or more fingerprints stored in a memory such as memory 730.

Figure 14C:
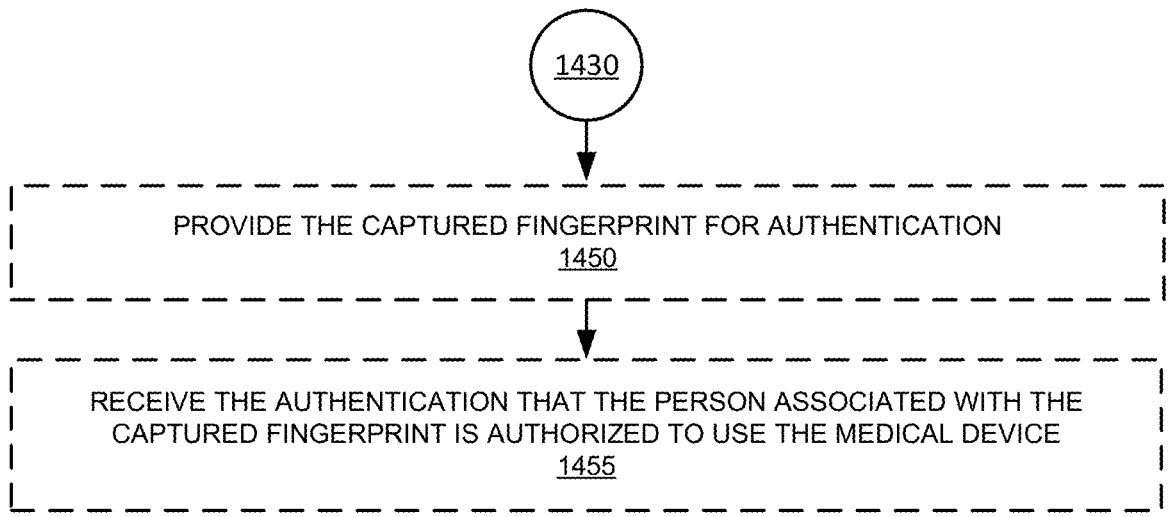

With reference to FIG. 14C, at procedure 1450 of flow diagram 1400, in various embodiments, the method as illustrated in FIG. 14A further includes providing the captured fingerprint for authentication. For example, processor 720 may provide a captured image of fingerprint 860 to processor 820 for authentication. In another embodiment, a captured image of fingerprint 860 may be sent to an entity external to the medical device 800 for authentication and the results (authenticated or not authenticated) may be received at the medical device 800 from the entity. For example, a wireline or wireless connection to the Internet may facilitate sending a captured fingerprint to a hospital for comparison to a fingerprint database. A response may be that the captured fingerprint has been identified and authenticated to use the medical device 800 and may include the identity of the person associated with the captured fingerprint.

With continued reference to FIG. 14C, at procedure 1455 of flow diagram 1400, in various embodiments, the authentication is received that the person associated with the captured fingerprint is authorized to use the medical device. A response received from the external entity may indicate that the captured fingerprint has been authenticated to use the medical device 800 and may include the identity of the person associated with the captured fingerprint. The authentication may be received by processor 820 or processor 720 and an appropriate action may be initiated in response to authentication or failure to authenticate.

Figure 14D:
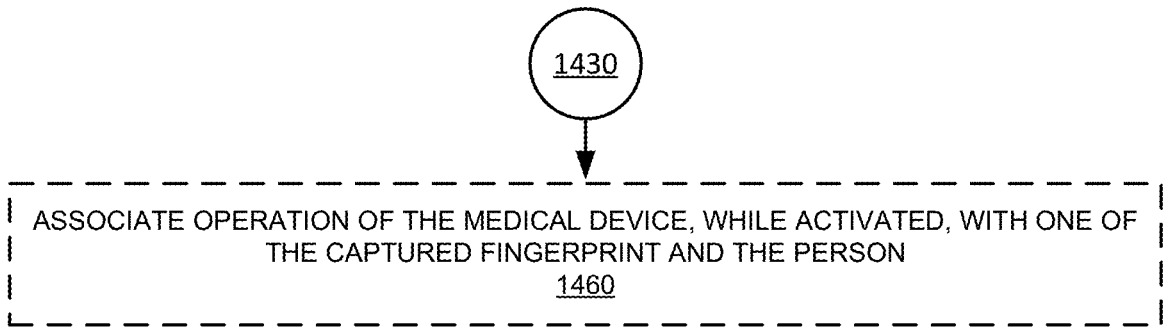

With reference to FIG. 14D, at procedure 1460 of flow diagram 1400, in various embodiments, the method as illustrated in FIG. 14A further includes associating operation of the medical device, while activated, with one of the captured fingerprint and the person. Put differently, the time period of operation of medical device 800 may be tagged or otherwise associated with the captured fingerprint or the name or other identity of the person associated with the captured fingerprint.

Figure 14E:

With reference to FIG. 14E, at procedure 1470 of flow diagram 1400, in various embodiments, the method as illustrated in FIG. 14A further includes associating a measurement made by the medical device, while activated, with one of the captured fingerprint and the person. Put differently, a measurement captured by medical device 800 may be tagged or otherwise associated with the captured fingerprint or the name or other identity of the person associated with the captured fingerprint. In some embodiments, the medical data is labeled or tagged with an identifier associated with the user. This identifier may be one or more of a number, name, codename, attribute of the captured fingerprint, or any other way to uniquely identify the user.

Figure 14F:

With reference to FIG. 14F, at procedure 1480 of flow diagram 1400, in various embodiments, the method as illustrated in FIG. 14A further includes determining a contact characteristic from the captured fingerprint.

The position of the finger, which finger is being used, the amount of contact surface, and the contact pressures are examples of contact characteristics that can be determined and monitored by fingerprint sensor 700. For one or more of these characteristics and/or to store a fingerprint a calibration procedure may be required. The calibration may comprise e.g., determining the best finger and/or the best position of a finger for the medical measurement, for example, with respect to features or structures of the finger such as e.g., blood vessels. Based on the contact characteristics a confidence factor or reliability factor of the medical measurement may be determined. The confidence factor may numerically express a level of confidence that the contact characteristic will facilitate successful collection of medical data with the medical device. The confidence factor may represent one or some combination of contact characteristics. The contact characteristics may be determined and monitored continuously during the medical measurement and the confidence factor may be also determined continuously and stored with the medical data (stream).

The position of the finger (e.g., finger 850) with respect to medical device 800 may be determined based on the captured fingerprint image, for example, by monitoring the center of the fingerprint 860 in the image. The pressure of a finger upon medical device surface 816 may be determined by measuring and monitoring ridges and valleys of a captured fingerprint. The contact area of a finger may be measured and monitored by determining a portion/percentage of an ultrasonic image captured by a fingerprint sensor 700 which is composed of ridges and valleys.

With continued reference to FIG. 14F, at procedure 1485 of flow diagram 1400, in various embodiments, the method as illustrated in FIG. 14A further includes employing the contact characteristic(s) to enable or disable the activation of the medical device. In some embodiments, even if captured fingerprint is authenticated, the medical measurements or activation of medical device 800 may only be performed if the contact characteristic(s) also indicates a confidence factor that exceeds a predetermined threshold. For example, if one or more of the fingers used, the position of the finger, the contact area of the finger, the contact pressure of the finger are not correct or meeting a confidence factor threshold, the medical device 800 may be deactivated, not activated, and/or a medical measurement may not be acquired. In other embodiments, when a confidence factor threshold is not exceeded, the user may be prompted to use a different finger, move the finger in a certain direction and/or a certain distance, apply more pressure, and/or apply less pressure as determined by the fingerprint sensor 700. In some embodiments, the medical measurement, may be adapted depending on the position of the finger, the adaptation may include ceasing the medical measurement, temporarily suspending it until the positioning is again within a suitable range of confidence factor.

FIGS. 15A-15F illustrate a flow diagram of an example method of operating a medical device, in accordance with various embodiments. Procedures of this method will be described with reference to elements and/or components of one or more of FIGS. 1A-13B. It is appreciated that in some embodiments, the procedures may be performed in a different order than described, that some of the described procedures may not be performed, and/or that one or more additional procedures to those described may be performed. Flow diagram 1500 includes some procedures that, in various embodiments, are carried out by one or more processors (e.g., sensor processor 720 of sensor processing unit 715 and/or host processor 820) under the control of computer-readable and computer-executable instructions that are stored on non-transitory computer-readable storage media (e.g., memory 730). When describing procedures of flow diagram 1500 reference will be made to components of medical device 800 (which may be either or both of medical devices 800A or 800B), however it should be borne in mind that the procedures may be similarly implemented with other medical devices, such as those described in FIGS. 10-13B. It is further appreciated that one or more procedures described in flow diagram 1500 may be implemented in hardware, or a combination of hardware with firmware and/or software. Additionally, it should be appreciated that the procedures are being described with respect to circuit boards and servers, however they may be implemented in other devices with cooling systems.

With reference to FIG. 15A, at procedure 1510 of flow diagram 1500, in various embodiments, a finger is detected in contact with a portion of the medical device. With reference to medical device 800, the portion may comprise medical device surface 816 and the contact may be detected by an ultrasonic fingerprint sensor 700 or by electrical sensors, capacitive sensors, pressure sensors, or other sensors coupled with medical device surface 816.

With continued reference to FIG. 15A, at procedure 1520 of flow diagram 1500, in various embodiments, responsive to detecting the finger, an ultrasonic sensor disposed beneath the portion of the medical device captures a fingerprint of the finger while the finger is in contact with the portion of the medical device. With reference to medical device 800, this may comprise ultrasonic fingerprint sensor 700 capturing an ultrasonic image of the fingerprint 860 of finger 850 while finger 850 contacts medical device surface 816.

The captured fingerprint may be identified as belonging to a particular person by comparison to stored and finding a match. This identification may be performed locally in medical device 800 by comparison to locally stored information. This identification may additionally or alternatively be performed remotely by communicating data of the captured fingerprint to an entity, such as a hospital patient system and database, which is external to medical device 800. If no match is found, then fingerprint is not identified as belonging to a particular person/patient.

With continued reference to FIG. 15A, at procedure 1530 of flow diagram 1500, in various embodiments, responsive to identifying a person associated with the captured fingerprint, operation of the medical device is activated. With reference to medical device 800 in FIGS. 8A and 8B, a processor, such as processor 720 or 820 may activate the operation of medical device 800.

In some embodiments, this comprises activating the operation of medical device 800 only for a duration of time that the finger 850 remains detected in contact with the portion (e.g., medical device surface 816) of medical device 800.

In some embodiments, this comprises activating the operation of medical device 800 upon verification that movement of the finger 850 is within a predetermined sufficient range of movement (such as having movement below a preset motion threshold) for the operation of medical device 800. A confidence factor and comparison to a threshold may be used to quantify and/or verify movement.

In some embodiments, this comprises activating the operation of medical device 800 upon verification that contact area of the finger 850 is sufficient for the operation of medical device 800 (e.g., the portion of fingerprint 860 detected/captured exceeds a predetermined area threshold and/or is within a desired area range). For example, this can be done be analyzing the portion or percentage of the ultrasonic image acquired by fingerprint sensor 700 that comprises a fingerprint image comprising a ridge/valley pattern. A confidence factor may be used to make this determination. A confidence factor and comparison to a threshold may be used to quantify and/or verify contact area.

In some embodiments, this comprises activating the operation of medical device 800 upon verification that contact pressure of the finger 850 is sufficient for the operation of medical device 800 (e.g., the portion of fingerprint 860 detected/captured exceeds a predetermined contact pressure threshold and/or is within a desired contact pressure range). The pressure of the finger on medical device surface 816 may be derived based on the changes of the ridge/valley pattern as the user puts down the finger. For example, when the pressure increases the valleys get smaller and the ridges get wider. The derived pressure may be compared to a pressure threshold to determine if the user is pressing hard enough on the medical device surface 816. A confidence factor and comparison to a threshold may be used to quantify and/or verify contact pressure.

In some embodiments, this comprises activating the operation of medical device 800 upon verification that position of finger 850 is sufficient for the operation of medical device 800 (e.g., the portion of fingerprint 860 detected/captured is properly positioned within some margin of error to receive a stick from a lancet or to contact a sensor). A confidence factor and comparison to a threshold or exemplar may be used to quantify and/or verify position.

In some embodiments, this comprises activating a conductive sensor to capture electrical measurements from finger 850, where the conductive sensor is disposed between the finger 850 and the ultrasonic fingerprint sensor 700 at the portion (e.g., the conductive sensor may be medical device surface 816) of the medical device 800. In some embodiments, this comprises activating a photoplethysmography device to obtain measurements from the finger. In some embodiments, this comprises activating an EKG device to obtain measurements from the finger. In some embodiments, this comprises activating a needle stick measuring device (e.g., a lancet) to protrude out of the medical device and into the finger and/or comprises activating the analysis of a captured blood sample.

Although an image of a fingerprint is described as being identified before medical device 800 is activated, in some embodiments, an image of a fingerprint may be captured while medical data is being measured and/or after medical data has ceased being measured. Either or both instances of additional capture may be conducted to further authenticate and validate that the medical data is associated with a single person throughout the measurement. During the operation of the medical device, the fingerprint sensor may also be operated in a mode different than the identification mode, for example to reduce required computing resources or power resources or to perform other functions. In some embodiments, the mode may be optimized to determine the contact characteristics of the finger, such as e.g., position, contact area, pressure, etc.

With reference to FIG. 15B, at procedure 1540 of flow diagram 1500, in various embodiments, the method as illustrated in FIG. 15A further includes the identifying of a person with the captured fingerprint. In some embodiments, the identifying may be performed by a processor, such as processor 720 or host processor 820 and may involve comparing data of a captured fingerprint to data of one or more fingerprints stored in a memory such as memory 730.

Figure 15C:
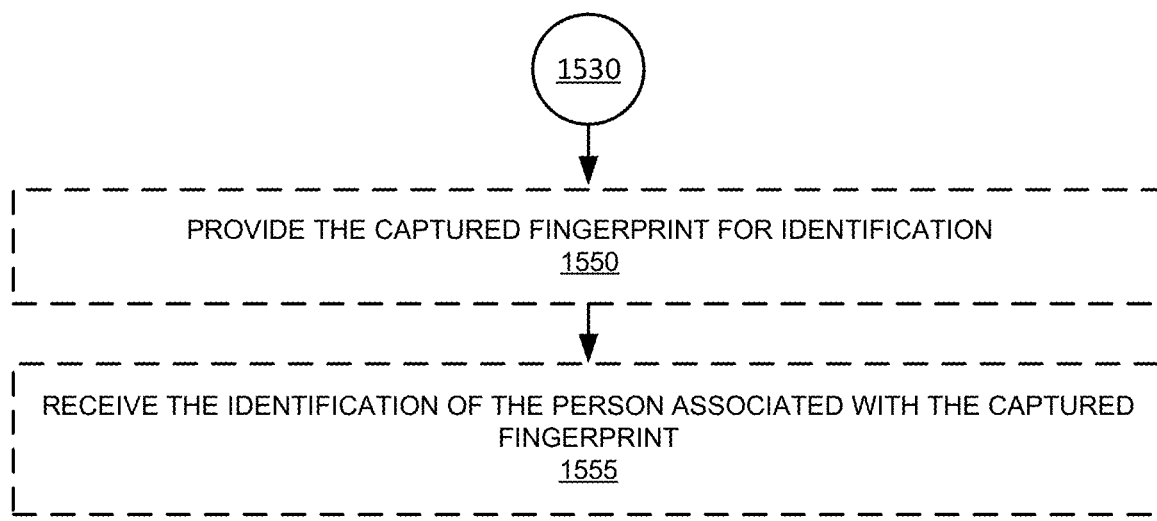

With reference to FIG. 15C, at procedure 1550 of flow diagram 1500, in various embodiments, the method as illustrated in FIG. 15A further includes providing the captured fingerprint for identification. For example, processor 720 may provide a captured image of fingerprint 860 to processor 820 for identification. In another embodiment, a captured image of fingerprint 860 may be sent to an entity external to the medical device 800 for identification and the results (identified or not identified) may be received at the medical device 800 from the entity. For example, a wireline or wireless connection to the Internet may facilitate sending a captured fingerprint to a hospital for comparison to a fingerprint database. A response may be that the captured fingerprint has been identified and may include the identity of the person associated with the captured fingerprint.

With continued reference to FIG. 15C, at procedure 1555 of flow diagram 1500, in various embodiments, identification of the person associated with the captured fingerprint is received. A response from the external entity may indicate that the captured fingerprint has been identified and may include the identity of the person associated with the captured fingerprint. The identification may be received by processor 820 or processor 720 and an appropriate action may be initiated in response to the identification or failure to identify.

Figure 15D:
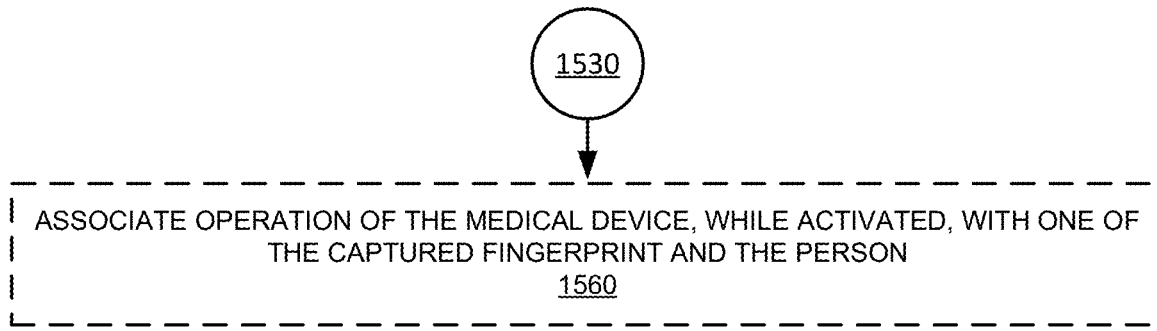

With reference to FIG. 15D, at procedure 1560 of flow diagram 1500, in various embodiments, the method as illustrated in FIG. 15A further includes associating operation of the medical device, while activated, with one of the captured fingerprint and the person. Put differently, the time period of operation of medical device 800 may be tagged or otherwise associated with the captured fingerprint or the name or other identity of the person associated with the captured fingerprint.

Figure 15E:

With reference to FIG. 15E, at procedure 1570 of flow diagram 1500, in various embodiments, the method as illustrated in FIG. 15A further includes associating a measurement made by the medical device, while activated, with one of the captured fingerprint and the person. Put differently, a measurement captured by medical device 800 may be tagged or otherwise associated with the captured fingerprint or the name or other identity of the person associated with the captured fingerprint. In some embodiments, the medical data is labeled or tagged with an identifier associated with the user. This identifier may be one or more of a number, name, codename, attribute of the captured fingerprint, or any other way to uniquely identify the user.

Figure 15F:

With reference to FIG. 15F, at procedure 1580 of flow diagram 1500, in various embodiments, the method as illustrated in FIG. 15A further includes determining a contact characteristic from the captured fingerprint.

The position of the finger, which finger is being used, the amount of contact surface, and the contact pressures are examples of contact characteristics that can be determined and monitored by fingerprint sensor 700. For one or more of these characteristics and/or to store a fingerprint a calibration procedure may be required. The calibration may comprise e.g., determining the best finger and/or the best position of a finger for the medical measurement, for example, with respect to features or structures of the finger such as e.g., blood vessels. Based on the contact characteristics a confidence factor or reliability factor of the medical measurement may be determined. The confidence factor may numerically express a level of confidence that the contact characteristic will facilitate successful collection of medical data with the medical device. The confidence factor may represent one or some combination of contact characteristics. The contact characteristics may be determined and monitored continuously during the medical measurement and the confidence factor may be also determined continuously and stored with the medical data (stream).

The position of the finger (e.g., finger 850) with respect to medical device 800 may be determined based on the captured fingerprint image, for example, by monitoring the center of the fingerprint 860 in the image. The pressure of a finger upon medical device surface 816 may be determined by measuring and monitoring ridges and valleys of a captured fingerprint. The contact area of a finger may be measured and monitored by determining a portion/percentage of an ultrasonic image captured by a fingerprint sensor 700 which is composed of ridges and valleys.

With continued reference to FIG. 15F, at procedure 1585 of flow diagram 1500, in various embodiments, the method as illustrated in FIG. 15A further includes employing the contact characteristic(s) to enable or disable the activation of the medical device. For example, even if captured fingerprint is identified, the medical measurements or activation of medical device 800 may only be performed if the contact characteristic(s) also indicates a confidence factor that exceeds a predetermined threshold. For example, if one or more of the finger used, the position of the finger, the contact area of the finger, the contact pressure of the finger are not correct or meeting a confidence factor threshold, the medical device 800 may be deactivated, not activated, and/or a medical measurement may not be acquired. In other embodiments, when a confidence factor threshold is not exceeded, the user may be prompted to use a different finger, move the finger in a certain direction and/or a certain distance, apply more pressure, and/or apply less pressure as determined by the fingerprint sensor 700. In some embodiments, the medical measurement, may be adapted depending on the position of the finger, the adaptation may include ceasing the medical measurement, temporarily suspending it until the positioning is again within a suitable range of confidence factor.

CONCLUSION

The examples set forth herein were presented in order to best explain, to describe particular applications, and to thereby enable those skilled in the art to make and use embodiments of the described examples. However, those skilled in the art will recognize that the foregoing description and examples have been presented for the purposes of illustration and example only. The description as set forth is not intended to be exhaustive or to limit the embodiments to the precise form disclosed. Rather, the specific features and acts described above are disclosed as example forms of implementing the claims.

Reference throughout this document to "one embodiment," "certain embodiments," "an embodiment," "various embodiments," "some embodiments," or similar term means that a particular feature, structure, or characteristic described in connection with the embodiment is included in at least one embodiment. Thus, the appearances of such phrases in various places throughout this specification are not necessarily all referring to the same embodiment. Furthermore, the particular features, structures, or characteristics of any embodiment may be combined in any suitable manner with one or more other features, structures, or characteristics of one or more other embodiments without limitation.

What is claimed is:
1. A medical device comprising:
  a sensing surface configured to interact with skin of a patient during operation of the medical device;
  an ultrasonic sensor disposed beneath the sensing surface and configured to ultrasonically measure data with respect to a region above the sensing surface both before and during acquisition of data by the medical device by passing ultrasonic signals back and forth through the sensing surface; and
  a processor coupled with the ultrasonic sensor, the processor configured to:
    responsive to detection of a finger in contact with the sensing surface, operate the ultrasonic sensor to capture a fingerprint of the finger from the ultrasonic signals passed back and forth through the sensing surface;
    determine a contact characteristic from the captured fingerprint;
    determine a confidence factor which numerically expresses a level of confidence that the contact characteristic will facilitate successful collection of medical data with the medical device;
employ the contact characteristic to enable or disable the activation of the medical device; and
responsive to authentication that a person associated with the captured fingerprint is authorized to use the medical device and the confidence factor exceeding a predetermined threshold, activate operation of the medical device.

2. The medical device of claim 1, wherein the processor is further configured to:
operate the ultrasonic sensor to detect the finger in contact with the sensing surface.

3. The medical device of claim 1, wherein the processor is further configured to:
authenticate that the person associated with the captured fingerprint is authorized to use the medical device.

4. The medical device of claim 1, wherein the processor is further configured to:
provide the captured fingerprint for authentication by an entity external to the processor; and
receive, from the entity external to the processor, the authentication that the person associated with the captured fingerprint is authorized to use the medical device.

5. The medical device of claim 1, wherein the sensing surface comprises a conductive electrode configured to capture electrical signals from the finger.

6. The medical device of claim 1, wherein the processor is further configured to:
associate operation of the medical device, after activation, with one of the captured fingerprint and the person.

7. The medical device of claim 1, wherein the processor is further configured to:
associate a measurement made by the medical device, after activation, with one of the captured fingerprint and the person.

8. A sensor processing unit comprising:
an ultrasonic sensor configured to ultrasonically measure data with respect to a region above a sensing surface of a medical device both before and during acquisition of data by the medical device, wherein the sensing surface is between the ultrasonic sensor and skin of a patient and is configured to contact the skin of the patient during operation of the medical device; and
a sensor processor coupled with the ultrasonic sensor, the sensor processor configured to:
responsive to detection of a finger in contact with the sensing surface, operate the ultrasonic sensor to capture a fingerprint of the finger by passing ultrasonic signals back and forth through the sensing surface;
determine from the captured fingerprint a contact pressure of the finger on the sensing surface; and
responsive to authentication that a person associated with the captured fingerprint is authorized to use the medical device and upon verification that the contact pressure of the finger is sufficient for the operation of the medical device, activate operation of the medical device.

9. The sensor processing unit of claim 8, wherein the sensor processor is further configured to:
operate the ultrasonic sensor to detect the finger in contact with the sensing surface.

10. The sensor processing unit of claim 8, wherein the sensor processor is further configured to:
authenticate that the person associated with the captured fingerprint is authorized to use the medical device.

11. The sensor processing unit of claim 8, wherein the sensor processor is further configured to:
provide the captured fingerprint for authentication by an entity external to the sensor processing unit; and
receive, from the entity external to the sensor processing unit, the authentication that the person associated with the captured fingerprint is authorized to use the medical device.

12. The sensor processing unit of claim 8, wherein the sensor processor is further configured to:
fuse an identifier of the person with medical data measured by the medical device, while activated.

13. A method of operating a medical device, the method comprising:
detecting a finger in contact with a portion sensing surface of the medical device;
responsive to detecting the finger, capturing, with an ultrasonic sensor disposed beneath the sensing surface of the medical device, a fingerprint of the finger while the finger is in contact with the sensing surface of the medical device both before and during acquisition of data by the medical device, wherein the capturing is accomplished by the ultrasonic sensor passing ultrasonic signals back and forth through the sensing surface of the medical device;
monitoring, via the ultrasonic signals, movement of the finger with respect to the sensing surface; and
responsive to authenticating that a person associated with the captured fingerprint is authorized to use the medical device and verification that movement of the finger with respect to the sensing surface is within a predetermined sufficient range of movement for the operation of the medical device, activating, by a processor, operation of the medical device.

14. The method as recited in claim 13, further comprising:
authenticating, by the processor, that the person associated with the captured fingerprint is authorized to use the medical device.

15. The method as recited in claim 13, further comprising:
providing, by the processor, the captured fingerprint for authentication; and
receiving, by the processor, the authentication that the person associated with the captured fingerprint is authorized to use the medical device.

16. The method as recited in claim 13, further comprising:
associating operation of the medical device, while activated, with one of the captured fingerprint and the person.

17. The method as recited in claim 13, further comprising:
associating a measurement made by the medical device, while activated, with one of the captured fingerprint and the person.

18. The method as recited in claim 13, further comprising:
determining a contact characteristic from the captured fingerprint; and
employing the contact characteristic to enable or disable the activation of the medical device.

19. The method as recited in claim 18, further comprising:
determining a confidence factor which numerically expresses a level of confidence that the contact characteristic will facilitate successful collection of medical data with the medical device.

20. The method as recited in claim 13, wherein the detecting a finger in contact with a sensing surface of the medical device comprises:

detecting, by the ultrasonic sensor, the finger in contact with the sensing surface of the medical device.

21. The method as recited in claim 13, wherein the activating, by a processor, operation of the medical device comprises:
   activating operation of the medical device only for a duration of time that the finger remains detected in contact with the sensing surface of the medical device.

22. The method as recited in claim 13, wherein the activating, by a processor, operation of the medical device further comprises:
   activating the operation of the medical device upon verification that contact area of the finger is sufficient for the operation of the medical device.

23. The method as recited in claim 13, wherein the activating, by a processor, operation of the medical device further comprises:
   activating the operation of the medical device upon verification that contact pressure of the finger is sufficient for the operation of the medical device.

24. The method as recited in claim 13, wherein the activating, by a processor, operation of the medical device further comprises:
   activating the operation of the medical device upon verification that position of the finger is sufficient for the operation of the medical device.

25. The method as recited in claim 13, wherein, activating operation of the medical device comprises:
   activating a conductive sensor to capture electrical measurements from the finger, the conductive sensor disposed between the finger and the ultrasonic sensor at the sensing surface of the medical device.

26. The method as recited in claim 13, wherein, activating operation of the medical device comprises:
   activating a photoplethysmography device to obtain measurements from the finger.

27. The method as recited in claim 13, wherein, activating operation of the medical device comprises:
   activating an electrocardiograph device to obtain measurements from the finger.

28. The method as recited in claim 13, wherein, activating operation of the medical device comprises:
   activating a needle stick measuring device to protrude out of the medical device and into the finger.

* * * * *